United States Patent
Ladisch et al.

(10) Patent No.: US 11,371,069 B2
(45) Date of Patent: *Jun. 28, 2022

(54) METHODS FOR MITIGATING THE INHIBITORY EFFECTS OF LIGNIN AND SOLUBLE PHENOLICS FOR ENZYMATIC CONVERSION OF CELLULOSE

(71) Applicant: Purdue Research Foundation, West Lafayette, IN (US)

(72) Inventors: Michael Ralph Ladisch, West Lafayette, IN (US); Young Mi Kim, Woodbury, MN (US)

(73) Assignee: Purdue Research Foundation, West Lafayette, IN (US)

( * ) Notice: Subject to any disclaimer, the term of this patent is extended or adjusted under 35 U.S.C. 154(b) by 127 days.

This patent is subject to a terminal disclaimer.

(21) Appl. No.: 16/937,055

(22) Filed: Jul. 23, 2020

(65) Prior Publication Data
US 2020/0392549 A1   Dec. 17, 2020

Related U.S. Application Data

(62) Division of application No. 15/541,531, filed as application No. PCT/US2015/066669 on Dec. 18, 2015, now Pat. No. 10,745,726.

(60) Provisional application No. 62/100,740, filed on Jan. 7, 2015.

(51) Int. Cl.
| C12P 19/14 | (2006.01) |
| C13K 1/02  | (2006.01) |
| C12P 19/02 | (2006.01) |

(52) U.S. Cl.
CPC ........... *C12P 19/14* (2013.01); *C12P 19/02* (2013.01); *C13K 1/02* (2013.01); *C12P 2201/00* (2013.01); *Y02E 50/10* (2013.01)

(58) Field of Classification Search
CPC ...... Y02E 50/10; C12P 2201/00; C12P 19/02; C12P 19/14; C13K 1/02
See application file for complete search history.

(56) References Cited

U.S. PATENT DOCUMENTS

| 6,620,292 B2   | 9/2003 | Wingerson |
| 2005/0065336 A1 | 3/2005 | Karstens |
| 2011/0076725 A1 | 3/2011 | Yang et al. |
| 2012/0070864 A1 | 3/2012 | Liu et al. |

FOREIGN PATENT DOCUMENTS

| CN | 101586136 A | 11/2009 | |
| CN | 103597085 A | 2/2014 | |
| WO | 2005/024037 A2 | 3/2005 | |
| WO | WO-2005024037 A2 * | 3/2005 | ............ C12P 19/02 |
| WO | 2009/032200 A1 | 3/2009 | |
| WO | 2010/029568 A2 | 3/2010 | |
| WO | WO-2010029568 A2 * | 3/2010 | ............ C12P 7/10 |
| WO | 2010/113130 A2 | 10/2010 | |
| WO | 2010/121348 A1 | 10/2010 | |
| WO | WO-2010121348 A1 * | 10/2010 | ............ D21C 1/02 |
| WO | 2013/165968 A1 | 11/2013 | |

OTHER PUBLICATIONS

Feb. 25, 2016—(WO) International Search Report—App PCT/US2015/066669.
Feb. 25, 2016—(WO) Written Opinion—App PCT/ US2015/066669.
May 18, 2018—(EP) Supplemental Search Report—App 15877338.2.
Dec. 27, 2019—(US) Non Final Office Action—U.S. Appl. No. 15/541,531.
Apr. 2, 2020—(CN) First Office Action & Search Report—App 201580076618.9.
Kim et al., "Enzymatic Digestion of Liquid Hot Water Pretreated Hybrid Poplar," Biotechnol. Prog., vol. 25, No. 2, pp. 340-348 (Mar. 17, 2009).
Kim et al., "Liquid Hot Water Pretreatment of Cellulosic Biomass," Methods in Mol. Biol., vol. 581, pp. 93-102 (Aug. 2009).
Yang et al., "BSA treatment to enhance enzymatic hydrolysis of cellulose in lignin containing substrates," Biotechnology and Bioengineering, vol. 94, No. 4, pp. 611-667 (Jul. 5, 2006).

* cited by examiner

*Primary Examiner* — Neil P Hammell
*Assistant Examiner* — Trevor Logan Kane
(74) *Attorney, Agent, or Firm* — Banner & Witcoff, Ltd.

(57) ABSTRACT

Disclosed herein are methods for improving ethanol production from biomass sources by blocking cellulose from binding to lignin.

20 Claims, 10 Drawing Sheets

METHODS FOR MITIGATING THE INHIBITORY EFFECTS OF LIGNIN AND SOLUBLE PHENOLICS FOR ENZYMATIC CONVERSION OF CELLULOSE

CROSS-REFERENCE TO RELATED APPLICATIONS

This application is a division of U.S. patent application Ser. No. 15/541,531 filed Jul. 5, 2017, which is a U.S. National Stage application under 35 U.S.C. § 371 of, and incorporates by reference in its entirety, International Application PCT/US2015/066669 (published as WO2016/111830), filed Dec. 18, 2015, which claims the benefit of priority to U.S. 62/100,740, filed on Jan. 7, 2015, the contents of which is incorporated by reference in its entirety into this disclosure.

STATEMENT GOVERNMENT INTEREST

This invention was made with government support under DE-AC36-98GO10337; DE-FC36-08GO18103; and DE-FG02-06ER64301 by the United States Department of Energy. The government has certain rights in the invention.

TECHNICAL FIELD

This disclosure relates to biomass to bioethanol conversion, and in particular to methods for improving ethanol production from biomass sources by blocking cellulose from binding to lignin.

BACKGROUND

This section introduces aspects that may help facilitate a better understanding of the disclosure. Accordingly, these statements are to be read in this light and are not to be understood as admissions about what is or is not prior art.

Hydrothermal pretreatments, such as liquid hot water pretreatment, steam explosion, and dilute acid pretreatment, enhance cellulolytic conversion of lignocellulose by solubilizing the hemicellulose fraction of the biomass. Due to the distinctively different pretreatment optima for hemicellulose and cellulose, a multi-stage pretreatment offers advantages over a single-stage pretreatment in terms of achieving a maximal recovery of both pentose and hexose sugars. In a multi-stage pretreatment, the first pretreatment can be optimized to remove the majority of hemicellulose while minimizing degradation of hemicellulose and re-precipitation of humins derived from the degradation. The subsequent pretreatments are more targeted to generate cellulose with enhanced susceptibility to cellulases.

The extent of hemicellulose removal alone is not a reliable parameter to predict enzymatic hydrolyzability of pretreated mixed hardwood. A great degree of variability in cellulose conversion yields existed among the pretreated hardwood materials even if majority of initial xylan was removed from the lignocellulose during liquid hot water pretreatment.

Given the integrative nature of the cell wall structure [67], pretreatment that changes one property will also affect others. Removal of hemicellulose and some lignin during liquid hot water pretreatment of lignocellulose, therefore, would also alter other substrate characteristics that affect cellulose hydrolyzability. The ease of enzymatic hydrolysis of cellulosic feedstocks can be affected by several substrate characteristics, such as cellulose's accessibility to cellulases which is a function of the degree of polymerization (DP), crystallinity, lignin and hemicellulose content and structure, and particle size.

Studies have investigated the effect of swelling, DP, fiber size, enzyme accessible area, crystallinity, composition, and presence of lignin on the enzymatic hydrolysis of various lignocellulosic materials. However, most studies involved measuring substrate characteristics of lignocellulose feedstocks that were either pretreated by different pretreatment technologies or pretreated within a limited range of pretreatment conditions.

There is therefore an unmet need for strategies to mitigate the inhibitory effects of lignin and soluble phenolics to ensure robust and economic enzymatic conversion of cellulose.

SUMMARY

In one aspect, a method for improving enzymatic digestibility of lignocellulose is presented. The method includes pretreating a lignocellulose feedstock and solubilizing hemicellulose in the lignocellulose feedstock. In another aspect, the lignocellulose feedstock has a composition of about 30 to about 60% cellulose, about 20 to about 40% hemicellulose, about 15 to about 30% lignin, with the balance extractives and ash to give a total of 100%. In yet another aspect, the method includes further includes separating and washing pretreated solids to thereby eliminate inhibition by soluble sugar-oligomers and phenolic compounds released during pretreating. In yet another aspect, the washing step further includes using water of between about 0.5 to about 15 times the weight of the biomass. In yet another aspect, the water is recycled water. In yet another aspect, the method further includes using distillation column bottoms.

In yet another aspect, the washing step is conducted at room temperature. In yet another aspect, the washing step is conducted at temperatures up to 100° C. In yet another aspect, the method further includes pressure washing at temperatures up to 140° C.

In yet another aspect, the washing step is carried out in at least two stages. In yet another aspect, the washing step further includes first using at a temperature of between about 50° C. and about 100° C. followed by water at 15 to 50 C.

In yet another aspect, the washing is carried out in a plurality of stages, wherein the washed solids from one stage is contacted counter-currently with wash water from a previous stage. In yet another aspect, the pretreating step includes a single-stage pretreatment. In yet another aspect, the pretreating step is conducted at temperatures above 140° C.

In yet another aspect, the pretreating step comprises a two-stage pretreatment. In yet another aspect, the first pretreating step is conducted at temperatures above 140° C. and the second pretreating step is conducted at temperatures above 180° C. In yet another aspect, the first pretreating step is conducted at temperatures above 140° C. and the second pretreating step is conducted at temperatures above 190° C. In yet another aspect, the first pretreating step is conducted at temperatures above 140° C. and the second pretreating step is conducted at temperatures above 195° C. In yet another aspect, the first pretreating step is conducted at temperatures above 140° C. and the second pretreating step is conducted at temperatures above 200° C. In yet another aspect, the first pretreating step is conducted at temperatures above 140° C. and the second pretreating step is conducted at temperatures above 205° C. In yet another aspect, the first pretreating step is conducted at temperatures above 140° C. and the second pretreating step is conducted at temperatures above 210° C.

In yet another aspect, the pretreating step includes a three-stage pretreatment. In yet another aspect, the first pretreating step is conducted at temperatures above 140° C. and the second pretreating step and third pretreating steps are conducted at temperatures above 180° C.

In yet another aspect, the pretreating step comprises a multi-stage pretreatment. In yet another aspect, the first pretreating step is conducted at temperatures above 140° C. and the subsequent pretreating steps are conducted at temperatures above 210° C.

In yet another aspect, the method further includes solubilizing at least half of the hemicellulose as xylo-oligosaccharides. In yet another aspect, the method also includes keeping the slurry under pressure to keep the water in a liquid state. The cellulose loading is between about 0.5 to about 40 FPU per gram glucan.

In yet another aspect, the method also includes blocking the lignin from binding with cellulose proteins with a non-specific binding protein. The pretreated solids are washed with 1 to 20 volumes of water per volume lignocellulose. In yet another aspect, the non-specific binding protein is bovine serum albumin (BSA). In yet another aspect, the pretreating step is conducted at a temperature of above 180° C.

In yet another aspect, the lignocellulose feedstock includes any one of or a combination of hardwood, corn stover, wheat straw, switchgrass, sugarcane bagasse, sorghum residues, corn pericarp, soybean hulls, soybean residue, hay, and/or softwoods.

In yet another aspect, a method is presented that includes solubilizing hemicellulose to thereby improve enzymatic digestibility of lignocellulose. The solubilizing step is accomplished by liquid hot water pretreatment. In yet another aspect, the liquid hot water pretreatment is carried at temperatures above 180° C. In yet another aspect, the liquid hot water pretreatment is carried out in multiple stages, such that the majority of hemicelluloses are preserved as xylo-oligosaccharides. In yet another aspect, the liquid hot water pretreatment comprises a single-stage pretreatment. In yet another aspect, the liquid hot water pretreatment is conducted at temperatures above 180° C.

In yet another aspect, the liquid hot water pretreatment comprises a two-stage pretreatment. In yet another aspect, the first pretreating step is conducted at temperatures above 140° C. and the second pretreating step is conducted at temperatures above 180° C. In yet another aspect, the first pretreating step is conducted at temperatures above 140° C. and the second pretreating step is conducted at temperatures above 190° C. In yet another aspect, the first pretreating step is conducted at temperatures above 140° C. and the second pretreating step is conducted at temperatures above 195° C. In yet another aspect, the first pretreating step is conducted at temperatures above 140° C. and the second pretreating step is conducted at temperatures above 200° C. In yet another aspect, the first pretreating step is conducted at temperatures above 140° C. and the second pretreating step is conducted at temperatures above 205° C. In yet another aspect, the first pretreating step is conducted at temperatures above 140° C. and the second pretreating step is conducted at temperatures above 210° C.

In yet another aspect, the pretreating step includes a three-stage pretreatment.

In yet another aspect, the first pretreating step is conducted at temperatures above 140° C. and the second pretreating step and third pretreating steps are conducted at temperatures above 180° C.

In yet another aspect, the pretreating step comprises a multi-stage pretreatment. In yet another aspect, the first pretreating step is conducted at temperatures above 140° C. and the subsequent pretreating steps are conducted at temperatures above 210° C.

In yet another aspect, the method further includes solubilizing at least half of the hemicellulose as xylo-oligosaccharides. In yet another aspect, the method further includes keeping the slurry under pressure to keep the water in a liquid state.

In yet another aspect, the method also includes a cellulase enzyme loading, wherein the cellulase enzyme loading is about 0.5 to about 20 FPU per gram glucan after the pretreatment is complete and temperature is reduced to below 70° C. In yet another aspect, the method also includes a cellulase enzyme loading, wherein the cellulase enzyme loading is about 0.5 to about 20 FPU per gram glucan after the pretreatment is complete and temperature is reduced to below 60° C. In yet another aspect, the method also includes a cellulase enzyme loading, wherein the cellulase enzyme loading is about 0.5 to about 20 FPU per gram glucan after the pretreatment is complete and temperature is reduced to below 50° C.

In yet another aspect, the method also includes blocking the lignin from binding with cellulose proteins with a non-specific binding protein. In yet another aspect, the non-specific binding protein is bovine serum albumin (BSA).

BRIEF DESCRIPTION OF DRAWINGS

FIG. 3A shows orange and blue dye adsorbed; Data is average of triplicate analysis. Error bars represent 95% CI. Numbers indicate different pretreatment conditions given in Table 1. UT indicates untreated wood, A untreated Avicel, and SF Solka Floc.

FIG. 3B shows total dye adsorbed and the ratio of orange dye to blue dye adsorbed. Data is average of triplicate analysis. Error bars represent 95% CI. Numbers indicate different pretreatment conditions given in Table 1. UT indicates untreated wood, A untreated Avicel, and SF Solka Floc.

FIG. 4A shows spezyme CP adsorption. Data is average of triplicate analysis. Error bars represent 95% CI.

FIG. 4B shows BSA adsorption. Data is average of triplicate analysis. Error bars represent 95% CI.

DETAILED DESCRIPTION

Figure 1:
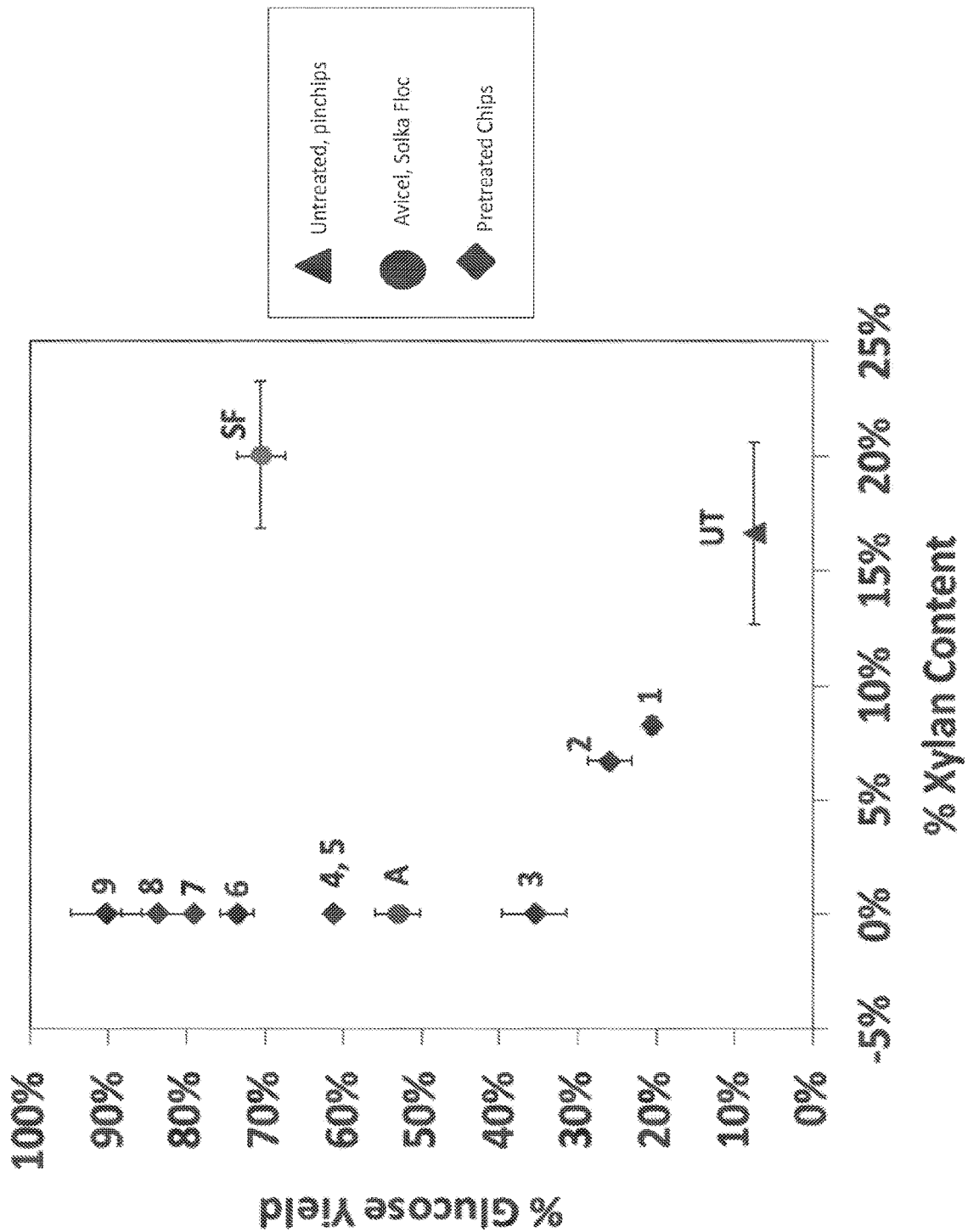
FIG. 1 is a plot showing the correlation between the percentage xylan remaining in pretreated, hot-water washed mixed hardwood and cellulose hydrolysis yields. Hydrolysis: 20 FPU (=32 mg protein) per g glucan, 50° C., 200 rpm, pH 4.8. Pretreatment conditions are given in Table 1. Data is average of triplicate analysis. Error bars represent 95% CI. Adapted from FIG. 4 in Kim et al. Numbers indicate different pretreatment conditions given in Table 1. UT indicates untreated wood, A untreated Avicel, and SF Solka Hoc.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In response to the unmet need, a method is disclosed herein that improves ethanol production from biomass sources by blocking cellulose from binding to lignin. To demonstrate the principles described herein, a common feedstock was pretreated at various severities to examine the changes of substrate characteristics and their attributes to the ease of hydrolysis. This enables investigation of the physicochemical changes of lignocellulose during liquid hot water pretreatment at varying conditions and determine the appropriate pretreatment conditions for efficient cellulose conversion by enzymes. Understanding lignocelluloses' structural and physicochemical changes during pretreatment and their effects on efficiency of enzymatic conversion of lignocellulose is critical for development of robust and cost-effect pretreatment technologies.

As disclosed herein, liquid hot water pretreatment improves enzymatic digestibility of lignocellulose by solubilizing hemicellulose which consequently opens up pores accessible by enzymes. However, complete removal of hemicellulose alone did not guarantee an efficient cellulose hydrolysis. Lignocellulosic materials must undergo structural and physical changes during the liquid hot water pretreatment to result in pretreated cellulose that is less recalcitrant to cellulase-catalyzed hydrolysis. Such substrate characteristics of mixed hardwood that were altered during liquid hot water pretreatment involved porosity (internal surface area), particle size (external surface area), and cellulose DP. Enzyme accessible pores and internal surface area are major yield-determining factors for the hydrolysis of pretreated mixed hardwood solids obtained from single stage pretreatments. Pretreatment at high temperature above 180° C. is beneficial as it creates more cellulase-accessible pores than pretreatment at a lower temperature of an equivalent severity factor. When pretreatment is carried out in multiple stages in order to solubilize and preserve the majority of hemicellulose as xylo-oligosaccharides without causing significant sugar degradation, enzyme accessible porosity or internal surface area is no longer a limiting factor that determines yields. For the multi-stage pretreated solids, external surface readily accessible by cellulases as well as cellulose DP played a major role in determining the ease of hydrolysis while internal porosity stays relatively constant over a wide range of pretreatment conditions.

High temperature pretreatments at above 200° C. either as a single or multi-stage pretreatments are needed to achieve efficient cellulose hydrolysis by generating cellulose substrates with increased external and internal surface area accessible by enzymes and low cellulose DP, all of which are favorable characteristics for overcoming recalcitrance of lignocellulose to enzymatic hydrolysis.

Inhibition by lignin remaining in pretreated wood that binds proteins in non-specific manner and which basically immobilizes cellulases away from the cellulose substrate, are major hurdles for cost-efficient hydrolysis of cellulose when a low-dose cellulase (3 mg protein/g cellulose) was applied. The presence of lignin restricts the amount of available cellulase for cellulose hydrolysis. The negative impact of lignin on cellulase intensifies as the cellulase loading approaches an economically-attractive level. Since hydrothermal pretreatments, such as liquid hot water, steam explosion, and dilute-acid pretreatments, retain the majority of initial lignin in the pretreated solids and release soluble phenolic compounds during the process, it is critical to develop strategies to mitigate the inhibitory effects of lignin and soluble phenolics to ensure robust and economic enzymatic conversion of cellulose.

As further described below, it is shown that the key requisites for the efficient hydrolysis of liquid hot-water pretreated lignocellulose include: 1) extensive solubilization of hemicellulose while minimizing sugar loss to degradation; 2) separation and washing of pretreated solids to eliminate inhibition by soluble sugar-oligomers and phenolic compounds released during pretreatments; 3) pretreatment conditions severe enough to cause substantial changes in substrate characteristics favorable for enzymatic hydrolysis, such as high internal and external surface area accessible by enzymes and low cellulose DP; 4) minimization of interaction of cellulase proteins with lignin retained in pretreated lignocellulose.

To demonstrate the principles described herein, the correlation between enzymatic digestibility and changes in substrate characteristics of the pretreated wood as measured by various analytical assays and methods is described in an Example. Among the number of different substrate characteristics associated with lignocellulose recalcitrance to enzyme hydrolysis, we measured cellulose porosity and enzyme accessible surfaces, cellulose particle size, and cellulose DP, which are major yield-determining factors. Crystallinity was not considered in this disclosure as it has been shown in many studies that there is no direct effect on the efficiency of enzymatic hydrolysis of lignocellulose. In addition, liquid hot water or dilute acid pretreatments increases crystallinity of cellulose as hemicellulose and some of lignin are solubilized during the pretreatment affecting the crystallinity measurement. This makes it complicated and difficult to relate the crystallinity with the ease of enzymatic hydrolysis. Lignin inhibition on hydrolysis is discussed as well and the effect of blocking lignin interaction with cellulase on hydrolysis at low enzyme dose is also reported.

As further disclosed herein, in one embodiment a method for improving enzymatic digestibility of lignocellulose is presented. The method includes pretreating a lignocellulose feedstock and solubilizing hemicellulose in the lignocellulose feedstock. In another aspect, the lignocellulose feedstock has a composition of about 30 to about 60% cellulose, about 20 to about 40% hemicellulose, about 15 to about 30% lignin, with the balance extractives and ash to give a total of 100%. In yet another aspect, the method includes further includes separating and washing pretreated solids to thereby eliminate inhibition by soluble sugar-oligomers and phenolic compounds released during pretreating. In yet another aspect, the washing step further includes using water of between about 0.5 to about 15 times the weight of the biomass. In yet another aspect, the water is recycled water. In yet another aspect, the method further includes using distillation column bottoms.

In yet another aspect, the washing step is conducted at room temperature. In yet another aspect, the washing step is conducted at temperatures up to 100° C. In yet another aspect, the method further includes pressure washing at temperatures up to 140° C.

In yet another aspect, the washing step is carried out in at least two stages. In yet another aspect, the washing step further includes first using at a temperature of between about 50° C. and about 100° C. followed by water at 15 to 50 C.

In yet another aspect, the washing is carried out in a plurality of stages, wherein the washed solids from one stage is contacted counter-currently with wash water from a previous stage. In yet another aspect, the pretreating step includes a single-stage pretreatment. In yet another aspect, the pretreating step is conducted at temperatures above 140° C.

In yet another aspect, the pretreating step comprises a two-stage pretreatment. In yet another aspect, the first pretreating step is conducted at temperatures above 140° C. and the second pretreating step is conducted at temperatures above 180° C. In yet another aspect, the first pretreating step is conducted at temperatures above 140° C. and the second pretreating step is conducted at temperatures above 190° C. In yet another aspect, the first pretreating step is conducted at temperatures above 140° C. and the second pretreating step is conducted at temperatures above 195° C. In yet another aspect, the first pretreating step is conducted at temperatures above 140° C. and the second pretreating step is conducted at temperatures above 200° C. In yet another aspect, the first pretreating step is conducted at temperatures above 140° C. and the second pretreating step is conducted at temperatures above 205° C. In yet another aspect, the first pretreating step is conducted at temperatures above 140° C. and the second pretreating step is conducted at temperatures above 210° C.

In yet another aspect, the pretreating step includes a three-stage pretreatment. In yet another aspect, the first pretreating step is conducted at temperatures above 140° C. and the second pretreating step and third pretreating steps are conducted at temperatures above 180° C.

In yet another aspect, the pretreating step comprises a multi-stage pretreatment. In yet another aspect, the first pretreating step is conducted at temperatures above 140° C. and the subsequent pretreating steps are conducted at temperatures above 210° C.

In yet another aspect, the method further includes solubilizing at least half of the hemicellulose as xylo-oligosaccharides. In yet another aspect, the method also includes keeping the slurry under pressure to keep the water in a liquid state. The cellulose loading is between about 0.5 to about 40 FPU per gram glucan.

In yet another aspect, the method also includes blocking the lignin from binding with cellulose proteins with a non-specific binding protein. The pretreated solids are washed with 1 to 20 volumes of water per volume lignocellulose. In yet another aspect, the non-specific binding protein is bovine serum albumin (BSA). In yet another aspect, the pretreating step is conducted at a temperature of above 180° C.

In yet another aspect, the lignocellulose feedstock includes any one of or a combination of hardwood, corn stover, wheat straw, switchgrass, sugarcane bagasse, sorghum residues, corn pericarp, soybean hulls, soybean residue, hay, and/or softwoods.

In yet another embodiment, a method is presented that includes solubilizing hemicellulose to thereby improve enzymatic digestibility of lignocellulose. The solubilizing step is accomplished by liquid hot water pretreatment. In yet another aspect, the liquid hot water pretreatment is carried at temperatures above 180° C. In yet another aspect, the liquid hot water pretreatment is carried out in multiple stages, such that the majority of hemicelluloses are preserved as xylo-oligosaccharides. In yet another aspect, the liquid hot water pretreatment comprises a single-stage pretreatment. In yet another aspect, the liquid hot water pretreatment is conducted at temperatures above 180° C.

In yet another aspect, the liquid hot water pretreatment comprises a two-stage pretreatment. In yet another aspect, the first pretreating step is conducted at temperatures above 140° C. and the second pretreating step is conducted at temperatures above 180° C. In yet another aspect, the first pretreating step is conducted at temperatures above 140° C. and the second pretreating step is conducted at temperatures above 190° C. In yet another aspect, the first pretreating step is conducted at temperatures above 140° C. and the second pretreating step is conducted at temperatures above 195° C. In yet another aspect, the first pretreating step is conducted at temperatures above 140° C. and the second pretreating step is conducted at temperatures above 200° C. In yet another aspect, the first pretreating step is conducted at temperatures above 140° C. and the second pretreating step is conducted at temperatures above 205° C. In yet another aspect, the first pretreating step is conducted at temperatures above 140° C. and the second pretreating step is conducted at temperatures above 210° C.

In yet another aspect, the pretreating step includes a three-stage pretreatment. In yet another aspect, the first pretreating step is conducted at temperatures above 140° C. and the second pretreating step and third pretreating steps are conducted at temperatures above 180° C.

In yet another aspect, the pretreating step comprises a multi-stage pretreatment. In yet another aspect, the first pretreating step is conducted at temperatures above 140° C. and the subsequent pretreating steps are conducted at temperatures above 210° C.

In yet another aspect, the method further includes solubilizing at least half of the hemicellulose as xylo-oligosaccharides. In yet another aspect, the method further includes keeping the slurry under pressure to keep the water in a liquid state.

In yet another aspect, the method also includes a cellulase enzyme loading, wherein the cellulase enzyme loading is about 0.5 to about 20 FPU per gram glucan after the pretreatment is complete and temperature is reduced to below 70° C. In yet another aspect, the method also includes a cellulase enzyme loading, wherein the cellulase enzyme loading is about 0.5 to about 20 FPU per gram glucan after the pretreatment is complete and temperature is reduced to below 60° C. In yet another aspect, the method also includes a cellulase enzyme loading, wherein the cellulase enzyme loading is about 0.5 to about 20 FPU per gram glucan after the pretreatment is complete and temperature is reduced to below 50° C.

In yet another aspect, the method also includes blocking the lignin from binding with cellulose proteins with a non-specific binding protein. In yet another aspect, the non-specific binding protein is bovine serum albumin (BSA).

Example

Materials and Methods:

Materials:

Hammer-milled mixed hardwood pin chips (average size of length and thickness of 0.5×0.1 cm) were provided by Mascoma Corporation (Lebanon, N.H.). Avicel PH101 and Solka Floc® 300FCC was purchased from Sigma-Aldrich (St. Louis, Mo.) and International Fiber Corporation (Urbana, Ohio), respectively. Spezyme CP (50 FPU/mL, 82 mg protein/mL, specific activity: 0.61 FPU/mg protein) was provided by Genencor, a Danisco Division (Palo Alto, Calif.). Novozym 188 (780 CBU/mL, 152 mg protein/mL) was purchased from Sigma (Cat. No. C6150). Cellic™ Ctec 2 (120 FPU/mL, 190 mg protein/mL, specific activity: 0.63 FPU/mg protein) was donated from Novozyme, North America Inc. (Franklinton, N.C.). Protein concentration of enzyme was determined by total nitrogen analysis after trichloroacetic acid (TCA) precipitation as described by Hames (1981). All other reagents and chemicals, unless otherwise noted, were purchased from Sigma-Aldrich (St. Louis, Mo.).

Compositional Analysis:

Composition of biomass solids was determined by NREL (National Renewable Energy Laboratory) LAP standard analytical procedures [21-23]. Analyzed components were glucan, xylan/galactan, arabinan, lignin, ash, and acetyl. The liquid fraction of the pretreated lignocellulose was analyzed for soluble mono- and oligosaccharides using LAP 014 [24]. Sugars were analyzed by HPLC as described below. All measurements were made in triplicate.

Pretreatment:

Conditions and apparatus for liquid hot water (LHW) pretreatment, as summarized by Kim et al. [1] were applied herein to pretreat the maple feedstock. Reactions were conducted in 1 in. OD×0.083 in. (2.54 cm 2.1 mm) wall thickness, 316 stainless steel tubing capped at either end with 1 in. (2.54 cm) Swagelok tube end fittings (Swagelok, Indianapolis, Ind.). Each tube was 4.5 in. (11.4 cm) in length and 45 mL in total volume. The sample volume was kept at 33.7 mL to give approximately 25% of head space for liquid expansion during heating to a target temperature. The aqueous pretreatment of mixed hardwood pinchips included mixing the substrate with DI water at 15% solids loading (w/w, g dry solids per g total) and pre-heating at 140° C. for 10 min, followed by heating at temperatures between 140 and 230° C. for 5 min to 19 hr including 5 min heat-up time. Pretreatment was done as a single-stage pretreatment or as two- or three-stage pretreatments. For multi-stage pretreatments, pretreated slurry from the previous stage was filtered and hot-water washed prior to the next pretreatment. Only the solid fraction was carried over to the subsequent pretreatment. Pretreatment conditions disclosed herein corresponded to severity factor (Log $R_0$) from 4.12 to 4.81 and summarized in Table 1. Pre-heat and pretreatment runs were all carried out in Tecam® SBL-1 fluidized sand baths (Cole-Parmer, Vernon Hills, Ill.) set to a target temperature. During the pretreatment, the slurry was under pressure in order to keep the water in a liquid state.

TABLE 1

Pretreatment conditions (temperature and time) of mixed hardwood pin chips.

| Symbol | Substrate | Temperature/Time | Severity (log $R_0$) |
|---|---|---|---|
| ▲ | UT Untreated. pinchips | n/a | n/a |
| ● | A Avicel PH101 | n/a | n/a |
|  | SF Solka Floc | n/a | n/a |
| ♦ | 1 Pretreated pinchips (1-ST PT) | 140° C./19 hr | 4.24 |
|  | 2 Pretreated pinchips (1-ST PT) | 160° C./5 hr | 4.24 |
|  | 3 Pretreated pinchips (1-ST PT) | 180° C./1.3 hr | 4.24 |
|  | 4 Pretreated pinchips (1-ST PT) | 200° C./0.33 hr | 4.24 |
|  | 5 Pretreated pinchips (2-ST PT) | 180° C./20 min ($1^{st}$ PT) 210° C./5 min ($2^{nd}$ PT) | 4.12 |
|  | 6 Pretreated pinchips (2-ST PT) | 180° C./20 min ($1^{st}$ PT) 220° C./10 min ($2^{nd}$ PT) | 4.59 |
|  | 7 Pretreated pinchips (3-ST PT) | 180° C./20 min ($1^{st}$ PT) 210° C./5 min ($2^{nd}$ PT) 210° C./30 min ($3^{rd}$ PT) | 4.81 |
|  | 8 Pretreated pinchips (3-ST PT) | 180° C./20 min ($1^{st}$ PT) 210° C./5 min ($2^{nd}$ PT) 220° C./15 min ($3^{rd}$ PT) | 4.81 |
|  | 9 Pretreated pinchips (3-ST PT) | 180° C./20 min ($1^{st}$ PT) 210° C./5 min ($2^{nd}$ PT) 230° C./7.5 min ($3^{rd}$ PT) | 4.81 |

After each pretreatment, the reactor tube containing the wood chip slurry was cooled by quenching in water for 10 min. The pretreated slurry was vacuum filtered using Whatman® No 1 filter paper to recover liquid and solid fractions for further analysis. Post-pretreatment washing of the pretreated solids was done as follows. The pretreated solids were mixed in 80-90° C. (hot) de-ionized water at 5% w/w dry solids. After 10 min of mixing, the slurry was filtered through a Whatman No. 1 filter paper. Pretreated, hot washed solids, pretreatment liquids and washates from each pretreatment were collected and analyzed for compositions as described above. All pretreatments were carried out in triplicate.

Enzymatic Hydrolysis:

High Enzyme Dose (20 FPU/g Glucan):

Untreated, pretreated solids of various severity factors, and pure cellulose (Avicel PH101 and Solka Floc) were enzymatically hydrolyzed by 20 FPU Cellic Ctec 2 per g glucan (=32 mg protein/g glucan) for 72 hr. Upon completion of the hydrolysis, the hydrolysate was boiled for 10 min to deactivate the enzymes.

Low Enzyme Dose (2 FPU/g Glucan):

Untreated, pretreated solids, and pure cellulose with or without bovine serum albumin (BSA) pre-incubation was hydrolyzed by 2 FPU Spezyme CP (=3 mg protein/g glucan) and 10 CBU Novozym 188 (equivalent to 2 mg protein) per g glucan for 168 hr. BSA treatment procedure is described in section 2.6.

Varying Enzyme Dose with BSA:

Pretreated, hot-washed solids sample 9 in Table 1 was hydrolyzed at varying total protein loadings (10-100 mg total proteins/g glucan) that combine BSA and cellulase. The amount of Spezyme CP was varied at each fixed total protein loading to give various ratio of cellulase to total proteins. Novozym 188 was added at 10 CBU/g glucan in all experiments. Hydrolysis was carried out for 168 hr.

All hydrolysis runs were carried out in triplicate at 1% w/v glucan loading, pH 4.8 to 5.0, 50° C. and 200 rpm, in an incubator-shaker. Samples were taken at the end of hydrolysis for analysis by HPLC. Error bars represent 95% CI of a mean.

Simon's Stain:

Simon's staining of lignocellulose was performed as described by Chandra et al. [25].

The concentrations of orange dye (DO) and blue dye (DB) in the supernatant from the centrifuge tube ($C_O$, $C_B$) were determined by solving the following two equations (1) and (2) (Lambert-Beer law for a binary mixture) simultaneously:

$$A_{455nm} = \varepsilon_{o/455}LC_o + \varepsilon_{B/455}LC_B \quad (1)$$

$$A_{624nm} = \varepsilon_{o/624}LC_o + \varepsilon_{B/624}LC_B \quad (2)$$

where $A_{455nm}$, $A_{624nm}$: absorbance of the mixture at 455,624 nm; $\varepsilon$: extinction coefficient of each component at the respective wave length (mL/mg·cm); L: 1 cm (cuvette width); C: concentration (mg/mL). The extinction coefficients were determined by preparing standard curves of each dye and measuring the slope of their absorbance at 455 and 624 nm. The extinction coefficient, $\varepsilon$, for high molecular weight orange dye was 51.5 at 455 nm and 0.243 at 624 nm. It was 2.62 and 14.5, respectively, for blue dye. All measurements were made in triplicate.

Cellulase and BSA Adsorption:

A commercial cellulase (Spezyme CP) or BSA was added to 2.5 g/L glucan of untreated, pretreated, and pure cellulose solution in pH 4.8 50 mM sodium citrate buffer at 150 mg protein/g glucan, and incubated for 1 hr at 25° C., 100 rpm in a reciprocating shaking incubator. The mixture was centrifuged at 10,000 rpm for 5 min and the protein concentration in the supernatant was measured using a Pierce BCA Protein Assay kit (Thermo Scientific, Rockford, Ill., Product No. 23225). Enzyme and BSA blanks were prepared without addition of cellulose samples. Substrate blanks included substrate and buffer only. The amount of protein adsorbed was calculated as the difference between the added amount of protein and the protein remaining in the supernatant after the incubation taking into account the absorbance contribution by the substrate controls. All measurements were made in triplicate.

Average Degree of Polymerization (DP) of Cellulose:

Cellulose DP was estimated from intrinsic viscosity of holocellulose samples. First, holocellulose samples were prepared as described in Hubbell and Ragauskas [26]. An aliquot of 2.5 g (o.d. wt) air-dried lignocellulose was dispersed into 200 mL DI water. Then, 1.5 mL of glacial acetic acid and 1.5 g of sodium chlorite (1.5 g) were added to the mixture. The mixture was heated in the shaking water bath at 70° C. for 2 hr. Every 2 hr, 1.5 mL of fresh acetic acid and 1.5 g of sodium chlorite were introduced for 6 hr. After 6 hr, the solid residue (holocellulose) was filtered out using a glass fiber filter and washed thoroughly with deionized water until the filtrate pH was neutral. The recovered holocellulose was air-dried and moisture content was measured. Intrinsic viscosity of the air-dried holocellulose was determined according to ASTM D1795 [27] using a Canon-Fenske glass capillary viscometer. Cellulose DP was then estimated based on the measured intrinsic viscosity of holocellulose by the following equation (3):

$$DP = \left(\frac{1.65 \cdot [\eta] - 116 \cdot H}{G}\right)^{1.11} \quad (3)$$

where [$\eta$] is the intrinsic viscosity (cm$^3$/g) of holocellulose and H and G are the mass fractions of hemicellulose and glucan in the lignin containing sample, respectively. All measurements were made in triplicate.

Wet Particle Size Determination:

Average particle size of wet pretreated and untreated pin chips was determined by sieving the material through mesh screens ranging from mesh size 2 (opening size 6 mm) to size 88 (0.04 mm). The sieving was carried out in water to keep the material wet. Wet solids collected on each sieve was recovered and dried in 105° C.' oven overnight and dry weight was measured. The average particle size was calculated according to Equation (4):

$$\Sigma_{d_p} d_p \cdot wt(d_p)\% \quad (4)$$

where $d_p$ is average particle diameter [cm] calculated as (sieve opening size, top-sieve opening size, below)/2 and wt ($d_p$)% is weight percentage of particles size of $d_p$. All measurements were made in duplicate.

TAPPI Useful Method UM 256 [29] was performed to determine water retention value of samples. A sample comparable to 1 g oven dry (o.d.) weight of never dried material was mixed in 100 mL DI water, filtered, and centrifuged at 900 g for 30 min at 24° C., followed by 105° C. oven drying for 3 hr. The water retention value is defined as below in Equation (5):

$$WRV = \frac{\text{wt of water retained in the sampe after centrifugation}}{\text{oven-dried wt of the sample}} \quad (5)$$

All measurements were made in triplicate.

HPLC:

Hydrolysis samples were analyzed by Bio-Rad Aminex HPX-87H ion exchange column (300 mm×7.8 mm, Bio-Rad Laboratories Inc., Hercules, Calif.) connected to a Milton Roy mini pump (Milton Roy Co., Ivyland, Pa.), Waters™ 717 plus autosampler, and Waters™ 2414 refractive index detector (Waters Corp., Milford, Mass.). The data was stored and processed using Empower™ 2 Chromatography Data Software (Waters Corp., Milford, Mass.). The mobile phase was 5 mM sulfuric acid in distilled, de-ionized water filtered to 0.2 μm. The mobile phase flow rate was 0.6 mL/min. The column temperature was maintained at 60° C. by an Eppendorf CH-30 Column Heater controlled by an Eppendorf TC-50 (Eppendorf, Westbury, N.Y.).

Results and Discussion:

Xylan Content Change in LHW Pretreated Mixed Hardwood:

We have shown that significant variability in hydrolysis yields exist among the materials pretreated at the same severity factor and glucose yields are correlated better with pretreatment temperature than with pretreatment severity

[6]. Also, we found that the enzymatic digestibility greatly varied even among the pretreated materials with the same extent of hemicellulose removal (see FIG. 4(B) in reference [6]). Hemicellulose removal is one of the major factors that contributes to the enhanced cellulose digestibility of liquid hot water pretreated lignocelluloses [1-3]. However, it is apparent that there are physicochemical changes other than xylan removal that directly affect the glucose yields during the hydrolysis of liquid hot water pretreated cellulose.

As also reported herein, we examined the selected pretreated mixed hardwood solids to study the key physicochemical characteristics of the substrates that directly affect cellulose hydrolysis. Out of the total 18 different pretreatment conditions conducted in Kim et al. [6], 9 different pretreatment conditions, which resulted in glucose yields ranging from 20 to 90%, were selected and analyzed for their changes in substrate characteristics. The sample designation and pretreatment conditions applied for these nine pretreated substrates are summarized in Table 1. Avicel and Solka Floc were chosen as non-lignin containing cellulose controls. Avicel was 100% cellulose and Solka Floc was 80% cellulose and 20% xylan as measured by NREL's LAP compositional analysis. Compositions of raw mixed hardwood and pretreated solids are summarized in FIG. 1 in Kim et al. [6]. Glucose yields of the untreated, pretreated mixed hardwood solids, and pure cellulose substrates were plotted against xylan content of the substrates in FIG. 1. The untreated mixed hardwood with 17% xylan content resulted in 8% glucose yield. The 1-stage pretreatment at 140 and 160° C. for 19 hr and 5 hr (Log $R_o$=4.24), respectively, solubilized 75-80% initial xylan, resulting in 7-8% xylan contents in the pretreated, washed solids. Glucose yields were improved only nominally to 21-26%. The pretreated, washed solids obtained at above 180° C. at the same severity factor (3, 4 in FIG. 1) contained no xylan and resulted in 36-61% glucose yields. Despite equivalent pretreatment severity and solubilization of all xylan, the pretreatment at 200° C. produced material that was significantly more hydrolysable than pretreated at 180° C. The pretreated, washed solids from the multi-stage pretreatments also contained no measurable xylan, yet the glucose yields greatly varied from 61 to 90%. Glucose yields of the untreated, non-lignin cellulose substrates, Avicel and Solka Floc were 53 and 71%, respectively.

It is clearly demonstrated that the major effect of liquid hot water pretreatment is to solubilize and remove xylan from the lignocellulose which appears to improve cellulose conversion of the pretreated materials. When there was remaining xylan in the pretreated solids, a lower xylan content led to a higher cellulose hydrolysis. However, solubilization of all of the xylan during the pretreatment did not necessarily correspond to any further increase in cellulose conversion. Significant variability in glucose yields existed among the pretreated solids with no measurable xylan content. Considering that the xylan removal is not the only factor affecting enzymatic hydrolysis of pretreated cellulose, these results prompted us to identify other pretreatment-induced changes in substrate characteristics that can be better correlated to the cellulose conversion yields. These characteristics of pretreated mixed hardwood solids and their changes during the liquid hot water pretreatment at different conditions are discussed below.

Changes in Porosity and Cellulose Accessible Surface Area of LHW Pretreated Mixed Hardwood:

Cellulose materials are porous substrates. Cellulase-accessible surface area is cited as one of the most important substrate characteristics governing the ease of enzymatic hydrolysis of lignocellulosic feedstocks, as shown by a good correlation between the cellulase-accessible surface area and cellulose enzymatic hydrolysis yield [10, 15, 31].

The physical accessible volume, surface area, or accessibility of cellulose to enzymes can be measured by a couple of different methods. As summarized by Wang et al. [32], these methods can be grouped into two categories. One approach involves probing molecules of known molecular weights and sizes to directly measure pore volume or surface area of a substrate accessible to those probing molecules. The other approach determines the accessibility indirectly by measuring adsorption of compounds of known sizes on a substrate.

As disclosed herein, both approaches can be applied to measure cellulose accessibility to enzymes. The porosity and cellulase accessibility of untreated and pretreated mixed hardwoods, as well as non-lignin cellulose controls were evaluated by water retention value (WRV) measurement, Simon's staining method, and adsorption by cellulase and bovine serum albumin (BSA). Water retention value measures water binding and swelling capacity of materials, which are related to materials' pore characteristics [33]. Simons' stain (SS) was performed to measure porosity and surface area of pretreated materials. Cellulase adsorption determines the accessibility of cellulase to the pretreated materials. On the other hand, BSA adsorption indicates the exposed surface area of lignin that can cause non-specific binding with cellulases.

Water Retention Value:

Water retention value (WRV) is a measure of substrate's swelling using water molecules as probing compounds to indirectly determine the porosity of a tested material. The major drawback of WRV measurement on determining pore characteristics of a lignocellulose is that water molecules are much smaller than cellulase enzymes, thus it fails to precisely predict cellulase-accessible pores and surface areas [32]. Also, it does not provide any information about pore size distribution of the tested material. Therefore, the WRV should be applied as a comparative and relative measure of swelling capacities of different substrates, not as a direct estimation of cellulase accessible pores and surface area of a specific material.

Despite these limitations, many studies have shown a linear correlation between WRV and susceptibility of cellulose hydrolysis [7, 13, 34, 35].

Figure 2:
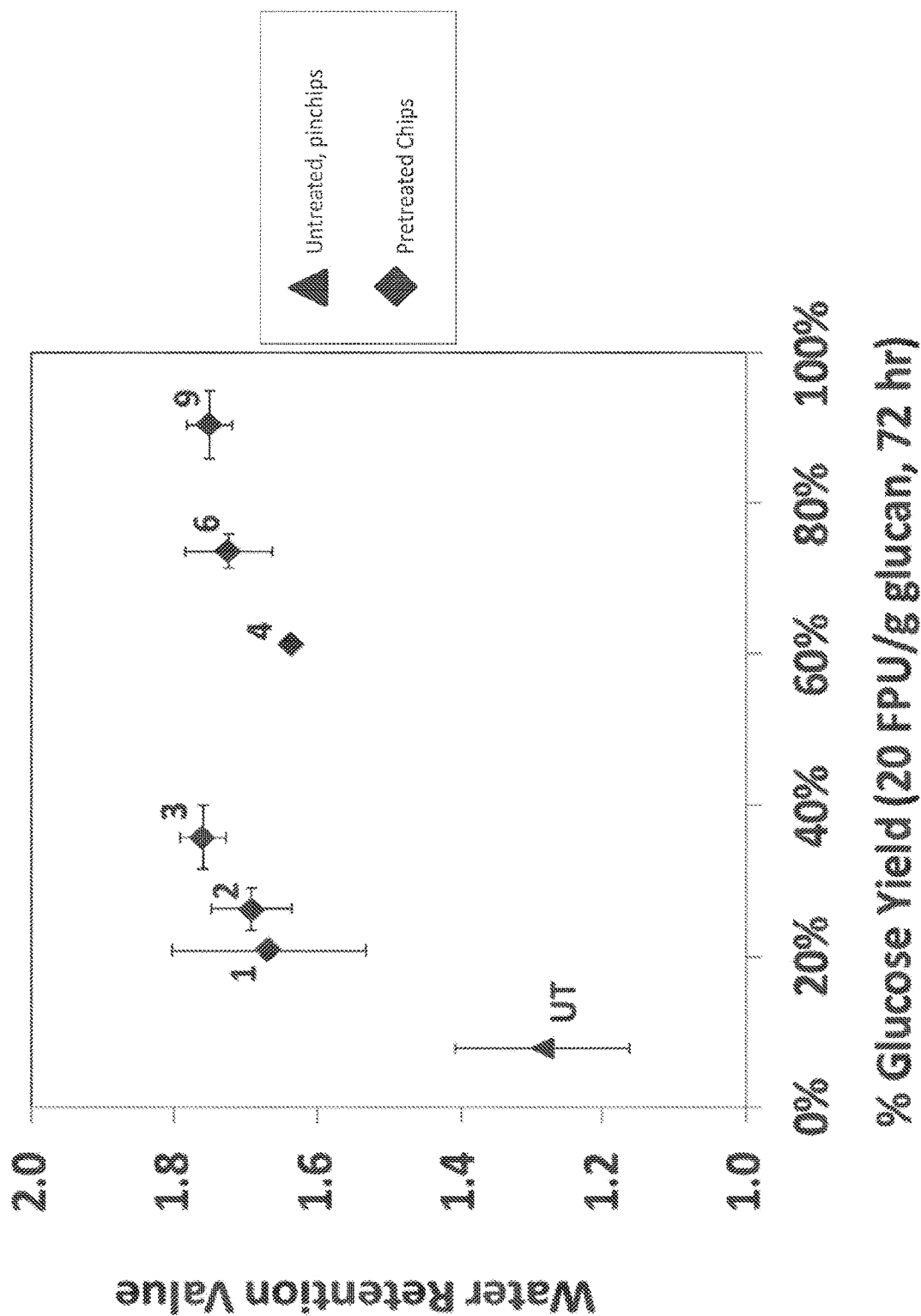
FIG. 2 shows the correlation between substrate porosity as measured by water retention value (WRV) and cellulose hydrolysis yields of pretreated, hot-water washed mixed hardwood. Data is average of triplicate analysis. Error bars represent 95% CI.

WRVs of raw and pretreated mixed hardwoods were measured and plotted against cellulose hydrolysis yields in FIG. 2 to see if water uptake capacity (swelling capacity) varied among the materials and how it correlated to the observed hydrolysis yields of cellulose. WRV of raw, untreated mixed hardwood was the lowest among the tested substrates as expected.

LHW pretreated clearly induced swelling of mixed hardwood. The pretreated, washed solids gave 1.3-1.4 times higher WRV than untreated wood. However, the swelling capacities did not correlate linearly with cellulose conversion yields. WRVs increased linearly with the corresponding glucose yield values only up to a certain point (WRV=1.8) and reached a plateau. Even for the materials that showed a linear correlation between WRV and glucose yields, the differences in WRVs between these materials were too low to be regarded as statistically significant. The results indicate that the pretreatments did not cause significant variations in the measured WRVs (swelling) despite the substantial variability in the pretreated solids' susceptibility to enzymatic hydrolysis.

Simon's Staining:

We applied Simon's staining as an alternate approach to better evaluate the porosity changes of mixed hardwood during pretreatments. Simon's staining is widely used as a measurement for assessing porosity of various lignocellulosic feedstocks. Simon's staining method is based on the competitive adsorption of two dyes of different sizes and affinities for cellulose [33]. High molecular weight orange dye (OD) has a higher affinity for cellulose than blue dye (BD) and can penetrate large pores (5-36 nm). Blue dye has a diameter of 1 nm and can only access small pores [33, 36]. Therefore, orange dye populates large pores of a cellulosic material by displacing blue dye which has lower affinity for cellulose, while small pores which are not accessible by orange dye are preferably penetrated by blue dye molecules. By measuring the amount of these two dyes adsorbed to a lignocellulosic material in an aqueous solution, porosity and distribution of large and small pores of the substrate can be easily estimated.

The amount of total dye adsorbed defines the total surface area (porosity), both internal and external. The total dye adsorbed indicates the changes in overall porosity of materials while the ratio of orange to blue dye represents the distribution of large to small pores of the measured total porosity. While the increase of total dye adsorbed indicates the overall increase of porosity and surface area of the substrate, it does not necessarily represent the pores or surface area that are actually accessible by cellulase enzymes. It has been established that the rate-limiting size of pores for effective hydrolysis of lignocellulosic materials is 4-9 nm (average. 5.1 nm), which is the size of cellulase enzymes [31, 37-39]. Therefore, cellulases can penetrate all of the pores that are accessible by the high molecular weight orange dye molecules (5-36 nm) as they are larger than the size of cellulases (4-9 nm). Although the Simon's staining does not provide a complete pore size distribution of a substrate, it gives a rough measurement of the cellulase-accessible pores and surface area. Chandra et al. [33] developed a modified Simon's staining technique and the method has shown a positive correlation between extent of hydrolysis and surface area in many studies [13, 14, 40, 41].

Figure 3A:
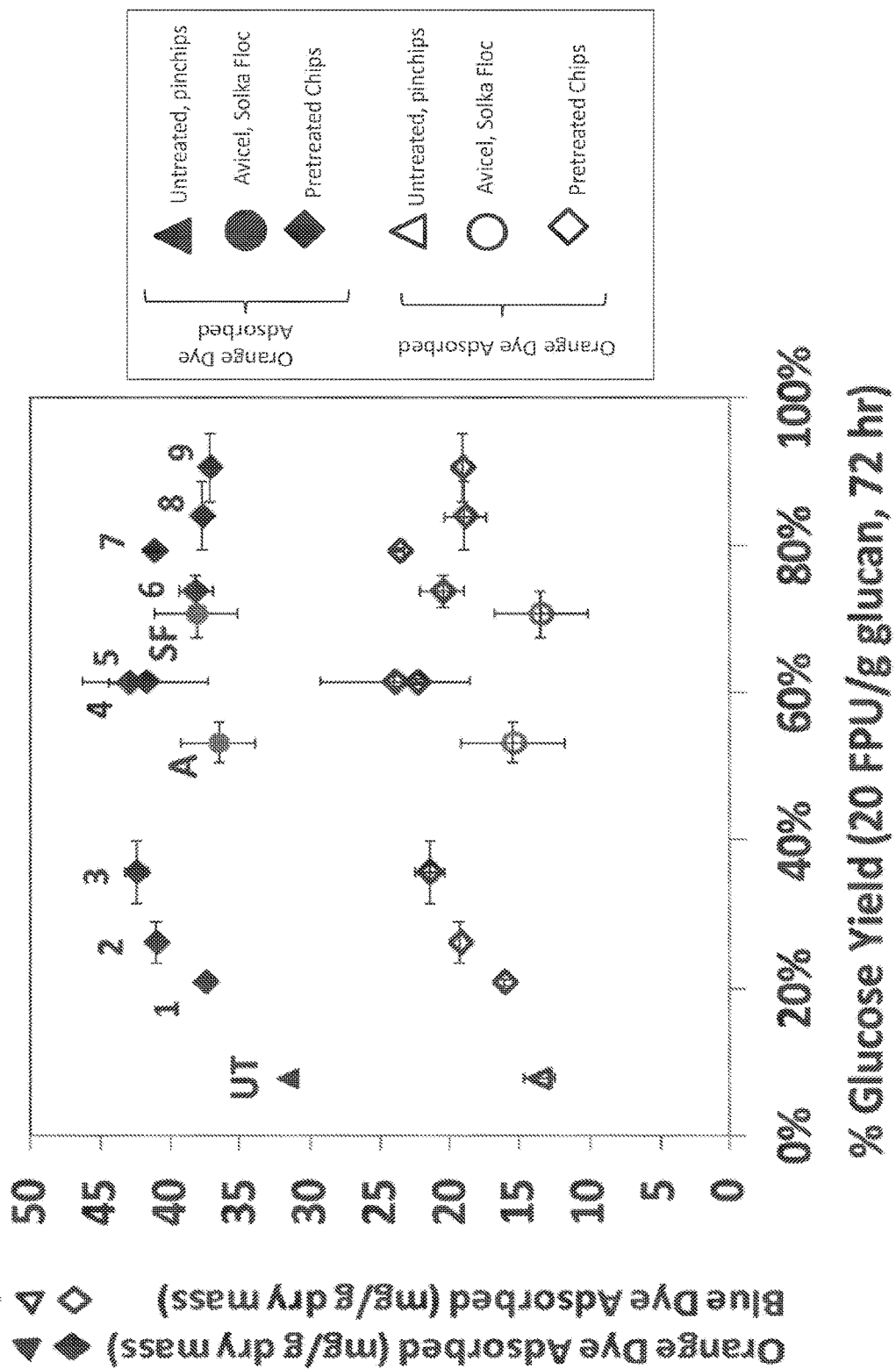
FIG. 3A show the correlation between porosity (total surface area) as measured by Simon's staining technique and cellulose hydrolysis yields of pretreated, hot-water washed mixed hardwood.
Figure 3B:
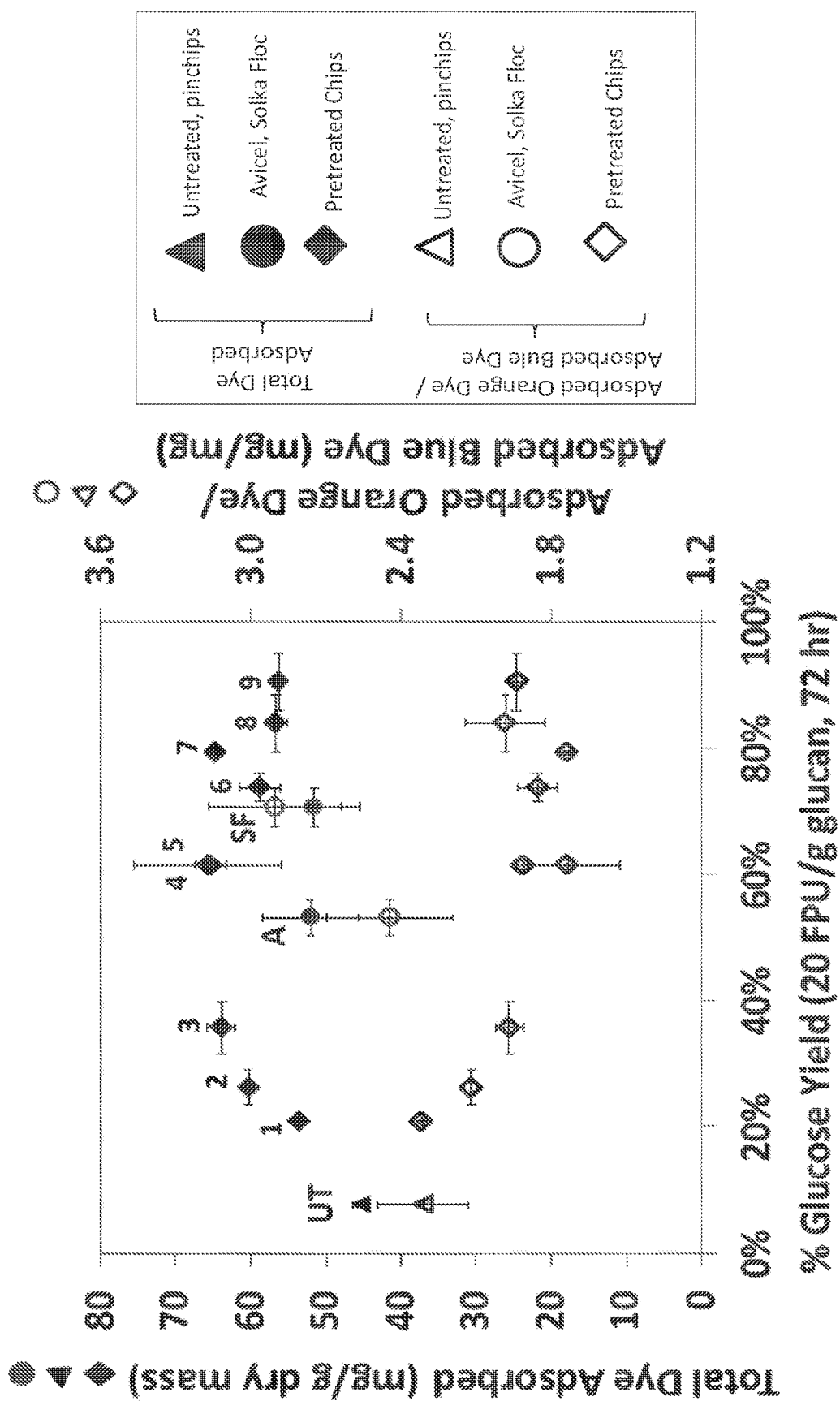
FIG. 3B shows the correlation between porosity (total surface area) as measured by Simon's staining technique and cellulose hydrolysis yields of pretreated, hot-water washed mixed hardwood.

FIGS. 3A and 3B show the correlation between the measured dye adsorption by Simon's staining and cellulose hydrolysis yields. The amounts of orange dye and blue dye adsorbed and the ratio of orange dye to blue dye were measured and plotted against the hydrolysis yields. Not surprisingly the amount of both orange and blue dyes adsorbed per unit dry mass of substrate was the lowest for untreated mixed hardwood (FIG. 3A). Consequently, the total dye adsorbed was also the lowest for the untreated material (FIG. 3B). Pretreatment increased the amount of both dyes adsorbed only to a certain extent and there was no further linear correlation between the dye adsorbed and cellulose hydrolysis yields. The porosity (total surface area) of the mixed hardwood increased by up to 45% from 45 mg to 65 mg total dye/g dry substrate (FIG. 3B).

For the single stage pretreatments corresponding to the pretreatment temperatures of 140-180° C. at severity factor of 4.24 (1, 2, and 3 in FIGS. 3A and 3B), a positive linear relation was found between the dye adsorbed and enzymatic hydrolysis of the pretreated solids. However, no clear statistically-significant correlation between the dye adsorbed and hydrolysis yields was observed for the multi-stage pretreatments (4-9 in FIGS. 3A and 3B). The amount of orange dye adsorbed for pure cellulose controls, Avicel and Solka Floc was in a similar range (36-38 mg orange dye/g dry mass) as that of pretreated wood chips. There was no significant difference in the amount of orange dye adsorbed between Avicel and Solka Floc, yet the hydrolysis yields were substantially different.

Overall, relating the total surface area as represented by the amount of total dye adsorbed with the extent of cellulose hydrolysis was mostly unsuccessful as shown in FIG. 3B. There was still no clear correlation between dye adsorbed and cellulose hydrolyzability when we only considered the amount of orange dye adsorbed which gives an estimate of cellulase accessible pores and surface area.

The ratio of adsorbed orange dye to blue dye (i.e., OD:BD) is often regarded as a better indicator of the enzyme-accessible surface area of cellulose than total dye adsorbed in the Simon's staining technique [14]. Studies have shown that a higher OD:BD ratio corresponded to a higher extent of cellulose hydrolysis for various feedstocks [13, 14, 40]. Unexpectedly, however, we found no clear correlation between the OD:BD and cellulose hydrolysis yields.

Contrary to other studies, the OD:BD decreased from 2.3 to 1.8 for the pretreated solids as their yield-responses increased (FIG. 3B).

The amount of each dye adsorbed needs to be considered when relating OD:BD to the extent of cellulose hydrolysis. When a substrate exhibits a decreased OD:BD after a pretreatment, it does not necessarily equate to cellulase-accessible pores having decreased or lower cellulose digestibility to enzymes. Hence correlating OB:BD with extent of cellulose hydrolysis should be interpreted in conjunction with both the amount of each dye and total dye adsorbed. A substrate may undergo a pretreatment that results in a material with lower OD:BD while exhibiting increased cellulase-accessible pores (increased amount of orange dye adsorbed) and susceptibility to cellulases. Such an example can be found when comparing the untreated wood chips and pretreated solids #5 in FIG. 3A. The amount of orange dye adsorbed for the sample 5 was 42 mg/g which was 31% higher than for the untreated substrate. This means that more cellulase-penetrable surface area is generated by the pretreatment. However, the pretreatment also increased small pores which are not accessible by cellulases as indicated by the amount of blue dye adsorbed. The increase of small pore caused by the pretreatment was greater (by 71%, from 14 mg to 24 mg per dry mass) than the increase of large pores as measured by orange dye (by 31%, from 32 to 42 mg per dry mass). As a result, the pretreated solids sample 5 resulted in a lower OD:BD (42 mg/24 mg=1.75) than the untreated (32 mg/14 mg=2.3), while its ease of hydrolysis was improved roughly by 10 times (from 7% to 61% glucose yield).

Cellulose and BSA Adsorption:

Another way to access the cellulase-accessible surface area is to determine cellulose adsorption capacity of a substrate by incubating the substrate with a known amount of cellulase proteins. Other authors have shown a good correlation between enzymatic digestibilities of lignocellulosic substrates with cellulose adsorption capacities [10, 11, 32].

Figure 4A:
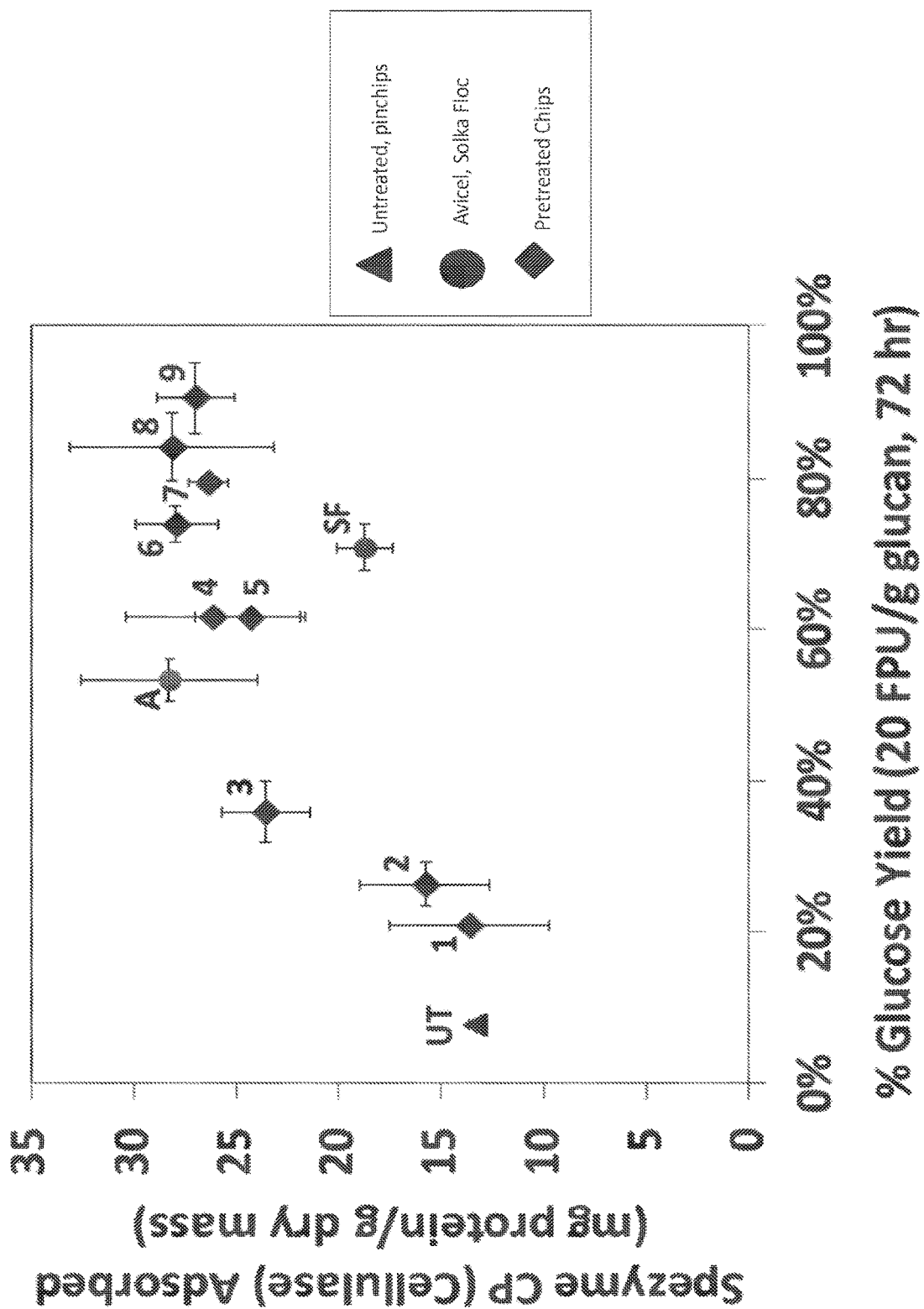
FIG. 4A shows the correlation between porosity (enzyme accessible surface area) as measured by protein (cellulase, BSA) adsorption and cellulose hydrolysis yields of pretreated, hot-water washed mixed hardwood.
Figure 4B:
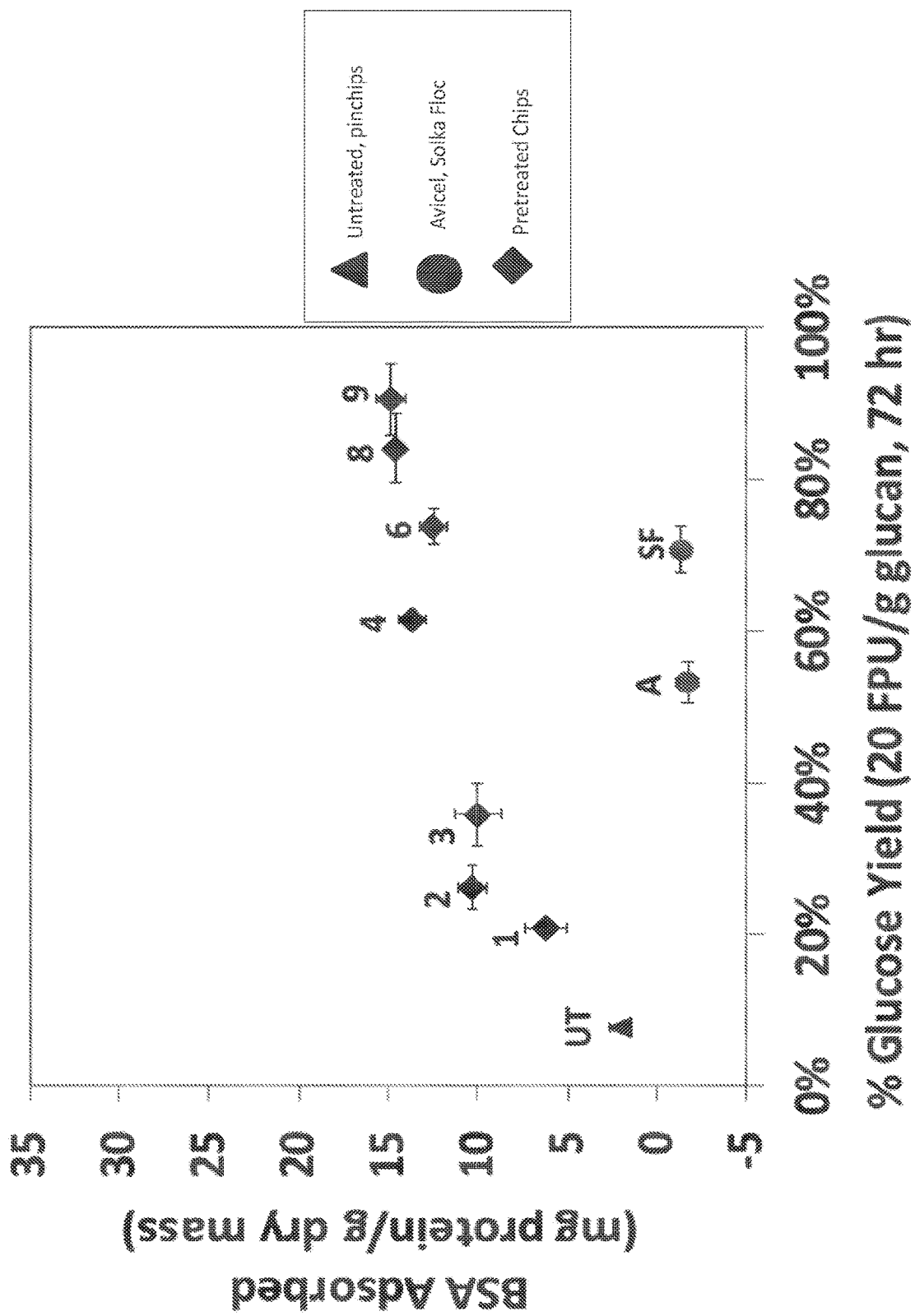
FIG. 4B shows the correlation between porosity (enzyme accessible surface area) as measured by protein (cellulase, BSA) adsorption and cellulose hydrolysis yields of pretreated, hot-water washed mixed hardwood.

A correlation between the cellulase accessible pores (or surface area) and cellulose digestibility to cellulase was determined by relating adsorbed cellulase enzymes with cellulose hydrolysis yields in FIG. 4A. Both mixed hardwood and non-lignin cellulose samples were incubated with an excess amount of Spezyme CP (150 mg protein/g glucan) for an hour at 25° C. and the protein in the supernatant was measured to calculate the amount of cellulase adsorbed.

The amount of cellulase adsorbed for untreated mixed hardwood was 13 mg protein/g dry mass, which was the lowest among the samples. Pretreatment increased the cellulase adsorption as much as 2.2 times (28 mg protein/g dry mass). Again, a positive linear relationship was found between the cellulose adsorption and cellulose digestibility for the pretreatment samples #1 to 3. For the other pretreated samples, there was no correlation between the cellulase adsorption and hydrolysis yields. The amount of Spezyme CP adsorbed reached the maximum at 26-28 mg per unit dry biomass for these pretreated samples as well as for Avicel. Solka Floc resulted in a lower amount of cellulose adsorbed (19 mg) than Avicel. Solka Floc has 20% hemicellulose in it vs. Avicel at 0%. Although average particle size of Solka Floc is smaller than Avicel (22 micron vs. 50 micron [64], the higher hemicellulose of Solka Floc likely leads to the lower adsorption.

All samples except for the non-lignin cellulose controls (Avicel, Solka. Floc) contain lignin to which cellulase can unproductively bind. The surface area specific to the unproductive binding of lignin to cellulose was estimated by incubating the samples with a non-specific binding protein, bovine serum albumin (BSA) at pH 4.8. BSA is known to block the non-productive binding of cellulose and improve enzymatic hydrolysis of cellulose [42]. BSA adsorption was plotted against cellulose digestibility in FIG. 4B. BSA did not bind to cellulose as indicated from the Avicel and Solka Floc in FIG. 4B. Untreated, raw mixed hardwood exhibited a very low (2 mg/g) BSA binding capacity. In comparison, pretreatment increased the amount of BSA binding up to 15 mg/g which was almost 7 times higher than that of the untreated mixed hardwood. Similar to the cellulase adsorption, a positive linear correlation between BSA and cellulose hydrolyzability was only found for the samples 1-4 and the BSA adsorption for the other pretreated solids was constant at 13-14 mg/g while the cellulose hydrolyzability varied significantly.

Consistent with the Simon's staining results, both cellulase and BSA adsorption exhibited a limited positive relationship with the ease of enzymatic cellulose hydrolysis. The cellulose-accessible surface area seemed to be in a close range for the pretreated solids with no measurable hemicellulose content (samples 4-9). Yet, the extent of enzymatic susceptibility of these pretreated solids was widely varied.

The results from WRV, Simon's staining, and protein adsorption indicate that liquid hot water pretreatment induces an increase of both total and cellulase accessible area as measured by these techniques, which corresponds to an enhanced cellulose digestibility to cellulases. We also found that the severity of liquid hot water pretreatment alone does not clearly relate to enzyme-accessible pores or surface area. This was clearly shown for the single stage pretreated samples, 1 through 4, all of which were prepared at the same pretreatment severity (Log $R_0$=4.24). At the same severity, a higher temperature created more pores and surface area penetrable by cellulases than a lower temperature pretreatment, resulting in a greater extent of cellulose hydrolysis by cellulases. When pretreatment was severe enough to solubilize all hemicelluloses and the resulting pretreated substrates are highly digestible by enzymes resulting in greater than 60% glucose yield with 20 FPU/g cellulose (32 mg/g), there were no obvious changes in porosity and cellulase-accessible area, yet the cellulose hydrolysis yields still differed significantly ranging between 60 to 90%. Our results suggest that enzyme-accessible surface area or porosity is a major yield-determining factor only for pretreated samples that still retain hemicellulose and exhibit relatively low enzymatic digestibilities. We find that the porosity is not the only factor that limits cellulose digestibility. Other substrate characteristics become yield-determining factors when liquid hot water pretreatment conditions are severe enough to solubilize the majority of hemicellulose and the resulting pretreated solids exhibit a relatively high digestibility by enzymes (>60% yield as measured using 20 FPU/g glucan cellulase).

Similarly, Ishizawa et al. [43] also found no significant correlation between substrate porosity and digestibility of cellulose in dilute-acid pretreated corn stover generated under varying pretreatment severities. They applied both solute exclusion method using a cellulase-sized molecule (5 nm) and $^1$H NMR thermoporometry to determine porosity and surface area accessibly by cellulases for the acid-pretreated corn stover. Consistent with our data, they found the biggest difference in the enzyme-penetrable pore volume occurs between untreated and pretreated corn stover. They failed to find significant differences in enzyme accessible pore volumes among the pretreated samples once the pretreated corn stover solids became highly digestible (>72% yield as measured with 20 mg protein/g cellulose of Spezyme CP after 7 days of simultaneous saccharification and fermentation).

Change in Particle Size (External Surface Area) of LHW Pretreated Mixed Hardwood:

Numerous studies have investigated the influence of particle size of lignocellulose on cellulose hydrolysis and indicated that particle size, absent other pretreatment, is a weak predictor of cellulose's susceptibility to enzymatic hydrolysis [8, 44, 45]. This suggests that reducing particle size of lignocellulose through mechanical pretreatment is insufficient to induce an efficient cellulose hydrolysis [45]. Studies have mainly focused on relating particle size of substrate with cellulose hydrolysis efficiencies. There has been no literature that clearly shows how particle size changes during hydrothermal pretreatments under different conditions and its effect on enzymatic susceptibility of the pretreated cellulose.

A smaller average particle size results in an increased external surface area where enzyme can readily act on. Thus, it could be expected that a correlation might exist between particle size and enzymatic hydrolysis of pretreated cellulose. Several studies have found a correlation between particle size and cellulose hydrolysis rates while the other studies found no clear relationship. For example, Arantes and Saddler et al. [14] reported that the exterior surface of lignocellulosic materials (corn stover, douglas fir, lodgepole pine, hybrid poplar) pretreated either by steam explosion or ethanol organosolv, did not influence the minimum requirement of enzymes for the effective enzymatic digestibility of the pretreated materials, while the total surface area measured by Simon's staining technique showed a clear positive correlation. They concluded that, based on their results, the hydrolysis of cellulose fibers occurs through cellulases penetrating large internal pores of cellulose materials causing disaggregation and fragmentation, rather than through an eroding or shaving action of cellulose surface by enzymes. Wang et al. [32] also suggested that the external surface contributes to cellulose hydrolysis much less than internal surface area. On the other hand, other studies provided evidence that support the importance of external surface area to cellulose digestion [18, 31]. Laivins and Scallan [46] have shown that fines have a higher pore volume than the other fiber fractions, with a linear correlation shown between fines content and the pore volume of mechanical pulp.

The porosity and cellulose-accessible surface area as measured by dye technique and protein adsorption may represent the combination of both external and internal total enzyme accessible area. On the other hand, particle size is an indicator of external surface area and it does not necessarily correlate with total enzyme accessible surface area. Two particles of different diameter and external surface area may display the same total cellulose-accessible surface area as determined by dye or protein adsorption discussed earlier. Not knowing how the external surface area of pretreated cellulose impacts the enzymatic digestibility makes it difficult to gauge the relative importance of internal (pores) versus external surface area on the efficiency of cellulose hydrolysis.

Figure 5:
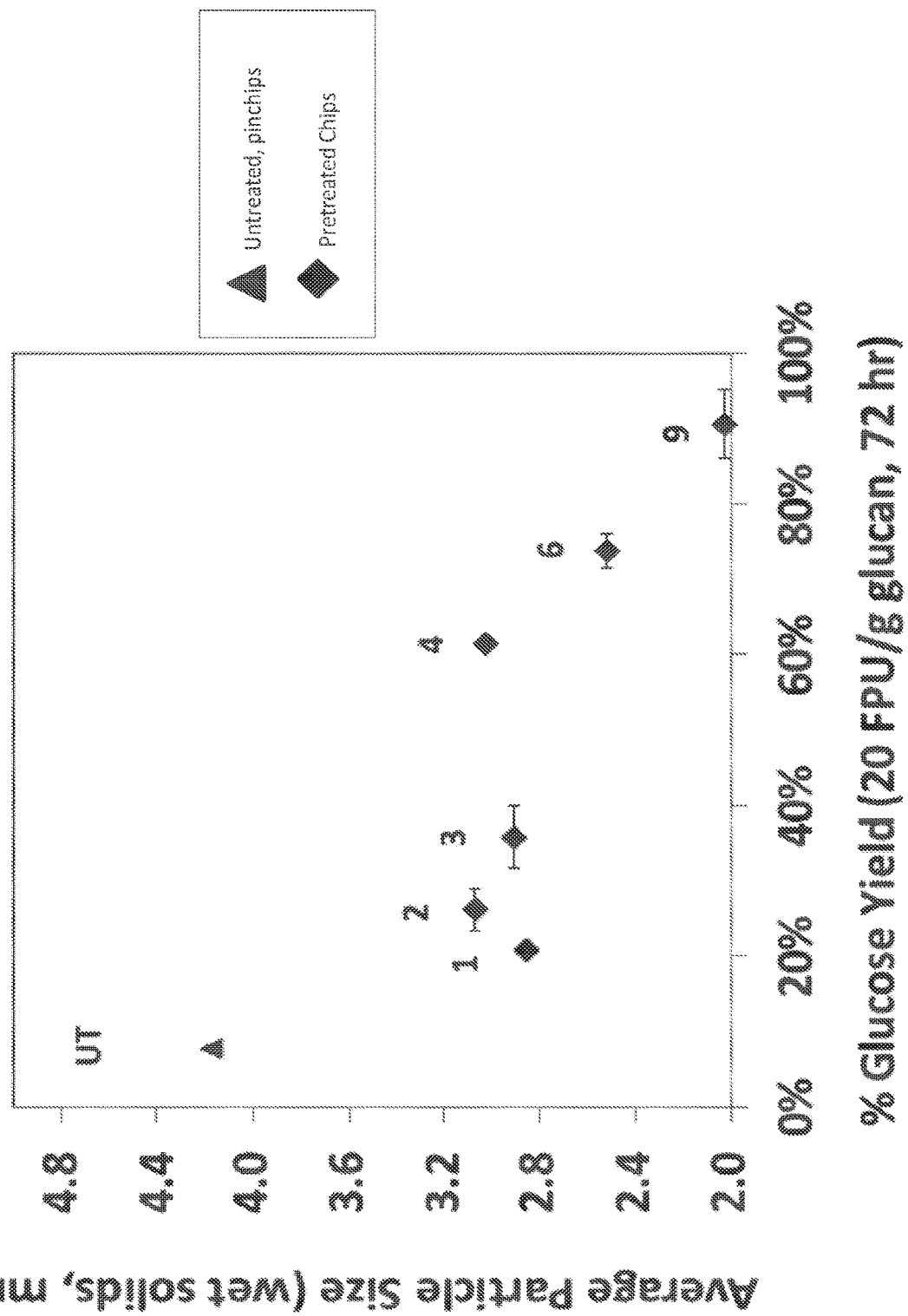
FIG. 5 shows the correlation between cellulose particle size (external surface area) and cellulose hydrolysis yields of pretreated, hot-water washed mixed hardwood. Data is average of triplicate analysis. Decrease in particle size correlates to higher conversion. Error bars represent 95% CI.

Average particle diameter of pretreated wood chips and raw mixed hardwood was measured and plotted against hydrolysis yields in FIG. 5. The particle size measurement using metal wired sieves was carried out while keeping the samples wet in water to prevent the materials from drying and shrinking. The average particle size of untreated mixed hardwood chips was 4.2 mm. Pretreatment reduced the average particle diameter by 30-70% depending on the severity of pretreatment. The differences in average particle size were negligible (2.9-3.1 mm) among the single-stage pretreated solids, samples 1-4, as shown in FIG. 5. The pretreated solids from the multi-stage pretreatments were greatly reduced in size (>50%) as compared to untreated and single-stage pretreated wood. Unlike the porosity measurements, which did not show any relationship with the cellulose enzymatic digestibility, a linear negative correlation was found between the particle size (external surface area) and glucose yield response of the cellulose hydrolysis for the pretreated solids with no measurable amount of xylan (samples 4-9). A smaller particle size of pretreated solids, which corresponds to a greater external surface area, led to enhanced cellulose hydrolysis yields. The amount of fines which are less than 0.3 mm diameter increased from 4.6% to 14% of the total mass for untreated solids compared to pretreated solids 9. More than 50% of the total untreated mixed hardwood had a diameter greater than 6 mm, while it was only 4% for the pretreated solids 9.

The results demonstrate that liquid hot water pretreatment disintegrates lignocellulose and reduces its average particle size. Increasing temperature up to 200° C. in a single-stage pretreatment did not induce much difference in average particle size (external surface area) among the samples. Yet, the porosity and cellulase-accessible surface area as measured by dye and protein adsorption increased significantly among these samples (1-4), with higher pretreatment severity resulting in more enzyme-accessible surface area than a lower severity.

This indicates that, for the single-stage pretreated solids (samples 1-4), porosity and internal surface area penetrable by enzymes play a major role in controlling cellulose hydrolysis as demonstrated in FIGS. 3A, 3B, 4A and 4B. External surface area has limited contribution to the cellulose hydrolysis efficiency of these samples that had been subject to single stage pretreatment.

Once all of the initial hemicellulose is solubilized during the first pretreatment, subsequent pretreatments at high temperature above 210° C. significantly reduce the particle size of lignocellulose. The pretreated solids from the multi-stage pretreatments (samples 4-9) exhibited similar total enzyme-accessible surface area (based on pore volume) as shown in FIGS. 3A, 3B, 4A and 4B, while the external surface area was substantially different among these substrates. A higher combined severity of multi-stage pretreatments generated a smaller average particle size and a greater external surface area of the pretreated cellulose. The external surface area of the multi-stage pretreated cellulose showed a direct relationship with the ease of cellulose hydrolysis.

These results indicate that external surface area readily accessible by enzymes becomes the yield-controlling factor of cellulose hydrolysis when pretreatment is severe enough to solubilize all hemicellulose.

High temperature (220° C.) dilute-acid pretreatment generated particles that were much smaller and hence have more external surface area relative to pretreatments at 180-200° C. The greater external surface area of high temperature dilute-acid pretreatment of mixed hardwood corresponds to a higher hydrolysis yield. Consistent with our results, this indicates that severe pretreatment at a high temperature above 200° C. generates smaller particles with greater external surface area which may be attacked more readily than the internal surface area of the enzyme accessible pores that are the predominant factor in increasing surface area at the lower temperature.

Burns et al, [31] also demonstrated that enzyme-sized pores of dilute acid pretreated mixed hardwood quickly disappeared at the initial stage of enzymatic hydrolysis and the enzyme-accessible surface in the later stage of hydrolysis mainly comes from external surface of cellulose fiber. Therefore, a smaller particle would experience less resistance to hydrolysis, not only at the initial stage of the hydrolysis but also as the hydrolysis progresses, leading to a higher cellulose conversion than a larger particle of a similar total enzyme accessible surface area. In addition, a larger particle size of lignocellulose material may experience a greater reduction in hydrolysis rates than a smaller particle as the hydrolysis reaction progresses due to the accumulation of more recalcitrant cellulose fraction and lignin blockage. During enzymatic hydrolysis of cellulose, easily accessible cellulose is first hydrolyzed while the amount of remaining, more resistant cellulose accumulates [47, 48]. Mooney et al. [49] also suggested that substantially reduced hydrolysis yields observed as the hydrolysis of cellulose proceeds might be caused by lignin restricting accessibility of enzymes to the remaining cellulose.

Our results indicate that internal surface area of pores accessible by enzymes for severely pretreated wood becomes is not as critical to the cellulose hydrolysis rates as it is for less severely pretreated lignocellulose. For hardwood, severely pretreated at above 200° C., reduction in particle size and increase of external surface area determines the extent of enzymatic hydrolysis of cellulose. A greater external surface area is expected to lead to a higher extent of cellulose hydrolysis since enzymes do not need to diffuse into the pores, while enzyme penetration into internal pores is a necessary step for a less severely, low temperature pretreated cellulose.

Cellulose DP Change in LHW Pretreated Mixed Hardwood:

The role of degree of polymerization (DP) on cellulolytic hydrolysis has been somewhat unclear and contradictory. Some studies have reported low DP cellulose hydrolyzed faster than high DP cellulose and other studies have found no clear relationship between DP and extent of enzymatic hydrolysis of cellulose [16, 50-52]. Del Rio et al. [52] and Puri [16] concluded that DP plays a significant role in controlling enzymatic hydrolysis of cellulose, showing that DP of various pretreated cellulose correlated negatively with cellulose conversion. Dilute sulfuric acid pretreatment of mixed hardwood at 180-220° C. has shown to decrease cellulose DP [53]. The reduction in the DP of cellulose leads to an improved cellulolytic hydrolysis of cellulose due to increased availability of cellulose chain ends for cellobiohydrolases to bind and the weakening of the aggregate hydrogen bond formation between cellulose chains allowing easier access of cellulases [54, 55].

Figure 6:
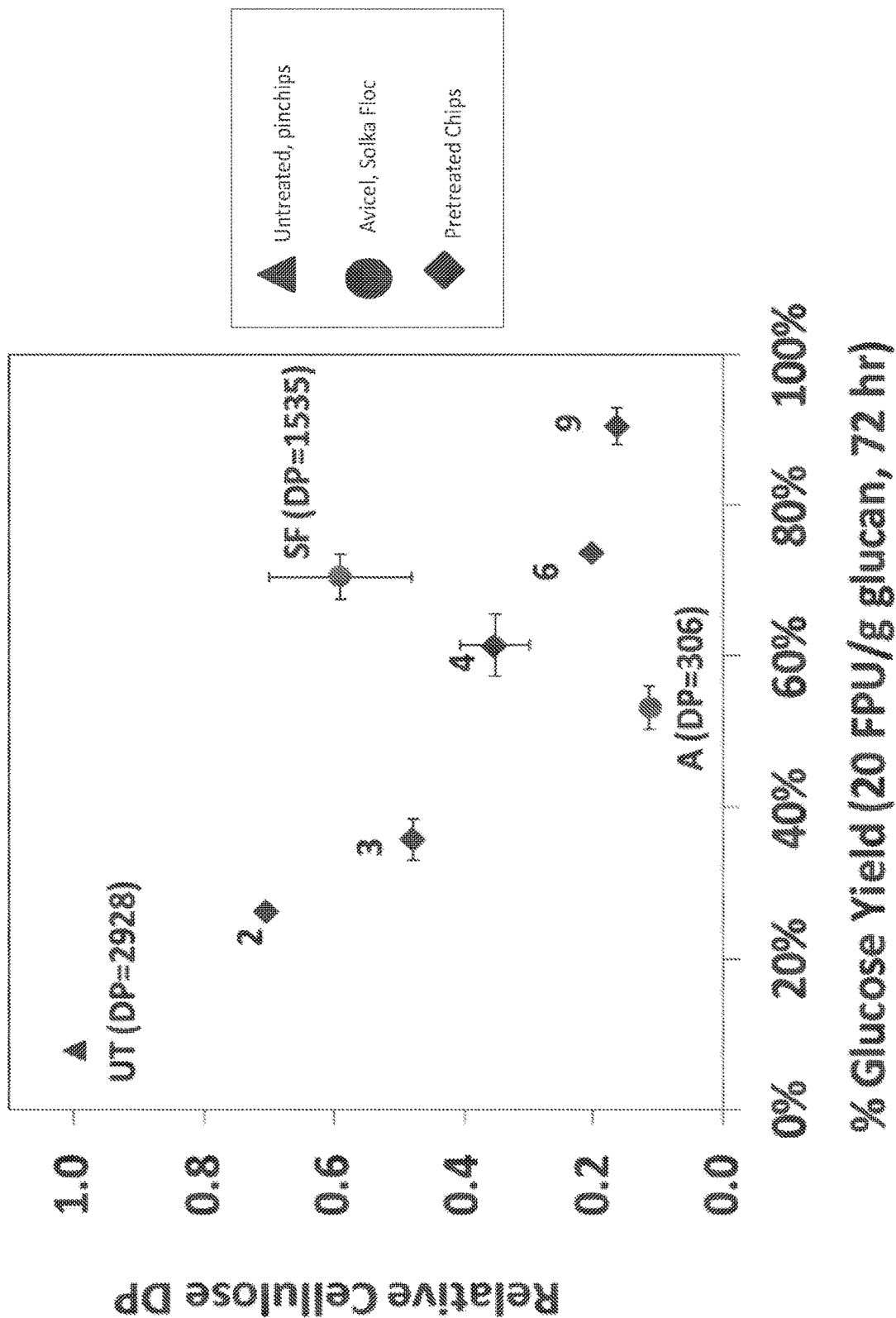
FIG. 6 shows the correlation between cellulose degree of polymerization (DP) and cellulose hydrolysis yields of pretreated, hot-water washed mixed hardwood. Data is average of triplicate analysis. Error bars represent 95% CI.

The DP values of cellulose in pretreated solids relative to untreated mixed hardwood cellulose were measured by viscometric method. These are summarized and plotted against cellulose conversion yields in FIG. 6. The viscosity average DP of untreated mixed hardwood pin chips was 2930, which was relatively close to the published viscometric DP values for various types of wood (3000-5000) [54]. Liquid hot water pretreatment significantly reduced the DP of cellulose. The pretreated solids sample 3 which was prepared at 180° C. for 1.3 hr (Log $R_0$=4.24) had a DP that was 50% lower than untreated hardwood. There was a clear linear drop of DP as the pretreatment temperature increased (sample #2 through 4) at a fixed severity factor. The multi-stage pretreatments resulted in an even further DP reduction and the reduction in the measured DP started to level off to a relative DP less than 0.2 (<600 to 1000). Sample 9 had the lowest DP which was equivalent to 16% of the DP of untreated cellulose and exhibited the highest cellulose yield. The average DP of Avicel and Solka Floc was 306 and 1535, respectively. The reported DP value of Avicel PH101 is 230 [68]. Despite the relatively high DP, Solka Floc was more digestible than Avicel. For the pure cellulose (Avicel, Solka Floc), cellulose DP was highly variable and did not correlate well with the cellulose conversion yields, suggesting that other factors such as crystallinity might play a major role on cellulose digestibility. Fan et al. [65] found that the hydrolysis rate is mainly dependent on cellulose crystallinity rather than surface area for Solka Floc and microcrystalline cellulose.

The cellulose DP was the only substrate characteristic examined herein that showed a clear correlation with the cellulose's susceptibility to cellulases for all pretreated samples of varying pretreatment conditions. We can conclude from the results that the liquid hot water pretreatment substantially reduces cellulose DP, and the DP reduction increases with the pretreatment temperature and severity until it reaches to a level-off DP (~500). In comparison, the level-off DP of sulfite wood pulps is between 200-400, for example [56]. The cellulose DP appeared to be one of the main determinants of cellulose conversion of liquid hot water pretreated wood in addition to the enzyme-accessible external and internal surface area and porosity as discussed earlier.

Effect of Blocking Lignin by BSA on Low Enzyme-Dose Cellulose Hydrolysis:

Despite the significant advances in cellulase effectiveness and cost in the past decade, cellulase cost is still the major cost factor in enzymatic conversion of lignocellulosics. Cost-efficient cellulose conversion cannot be realized without substantial reduction in enzyme dose. The enzyme dose commonly applied in most studies is in a range of 5-30 FPU/g glucan which is equivalent to 8-45 mg protein/g glucan, assuming 1.5 mg protein/FPU of a commercial cellulase. A figure of merit is given by corn to ethanol processes, where enzyme doses are 0.1-0.2% of dry corn weight and correspond to a loading of 1-2 mg protein/g dry corn [57]. For cellulosic ethanol process to be cost-effective, the cellulase (protein) dose must be similar. However, as cellulose loading approaches this low level, the ratio of phenolic-based inhibitors to enzyme proteins increases and may cause a significantly reduced cellulose hydrolysis through non-productive binding between phenolics and enzyme proteins [58]. Such phenolic-based cellulase inhibitors include both soluble phenolic compounds released during pretreatments [58-61] as well as lignin retained in the pretreated solids [62, 63]. It appears that β-glucosidase is especially sensitive to phenolics-induced inhibition by forming non-productive binding with phenolic compounds [58-60]. Furthermore, lignin is known to adsorb cellulases, and our work shows binding is likely to be non-specific at pH 5, which is slightly higher than the iso-electric pH of cellobiohydrolases I (pI=3.6-3.9), the most abundant cellulase in *Trichoderma reesei* [66]. As a means to alleviate the phenolic-induced inhibition, many studies used exogenous proteins to block lignin from binding with cellulases. Such proteins include albumin, BSA or peptone [42, 63]. For example, Pan et al. [63] reported that the cellulose conversion of steam-exploded softwood improved by as much as twice that of a control run when pretreated solids were treated with bovine serum albumin (BSA) or peptone.

As disclosed herein, the low cellulase dose cellulose hydrolysis of pretreated mixed hardwood solids was carried out using 3 mg cellulase protein (equivalent to 2 FPL Spezyme CP) per g glucan with or without BSA treatment (150 mg BSA/g glucan) to assess the impact of lignin inhibition on low-enzyme dose hydrolysis. Glucose yields of the low-dose cellulase hydrolysis with or without BSA treatment were plotted against the yields from high cellulase loading hydrolysis runs in FIG. 7A. As expected, BSA treatment did not affect the hydrolyzability of the non-lignin cellulose Avicel and Solka Floc as they do not contain lignin to adsorb BSA or cellulase protein (see FIG. 4B).

While >90% glucose yield was achieved for the most severely pretreated mixed-hardwood (sample 9) with the high cellulase loading at 20 FPU (=32 mg protein) per g glucan, the yield was only 13% when hydrolyzed with 1/10 cellulase dose (3 mg protein/g glucan). It was notable that glucose yields at low enzyme dose did not vary much (8-13% yield) among the pretreated solids while there was a great degree of variability in yields (20-90% yield) when a high dose of cellulase was used for hydrolysis of the same materials. This implies that the inhibition by non-productive binding between lignin and cellulase is amplified as the cellulase loading drops and the amount of cellulase available for cellulase is reduced. This consequently led to a low glucose yield (<15%) even for the severely pretreated materials which exhibited favorable substrate features for cellulose conversion, such as negligible xylan content, low cellulose DP, high external and internal cellulose-accessible surface area. The results suggest that efficient cellulose hydrolysis with low enzyme loading will be limited by non-favorable interactions between cellulase and lignin remaining in pretreated solids, even if the pretreated cellulose presents favorable physicochemical characteristics for cellulase accessibility. When cellulase was used at a high dosage, the inhibitory effect of lignin on cellulose hydrolysis was not as obvious since there was an excess amount of cellulase proteins present enough to overcome the inhibitory effect of lignin.

Cellulose conversion yields of the pretreated materials increased up to 70% when the pretreated materials were treated with BSA to block the lignin from binding with cellulase proteins. Also, the yield response of low cellulase dose hydrolysis runs showed a linear relationship with the yield response of high enzyme dose experiments. The pretreated solids exhibiting a low glucose yield with high enzyme dose also gave a low yield with $1/10^{th}$ lower enzyme dose, even when lignin was blocked from binding with cellulases by BSA treatment. On the other hand, highly digestible pretreated solids with 20 FPU cellulose per g glucan resulted in a greatly improved yield at $1/10^{th}$ of enzyme dose when pre-incubated with BSA. Once the inhibitory effect of lignin is eliminated by pre-incubating the pretreated solids with BSA, the cellulose conversion yields of pretreated wood with low enzyme dose responded in accordance with the structural characteristics of pretreated solids: cellulose DP, external surface area, porosity, and hemicellulose content. The results above show that minimizing inhibition by lignin and phenolic compounds is a key requirement for achieving cost-effective lignocellulose hydrolysis with cellulases.

Figure 7A:
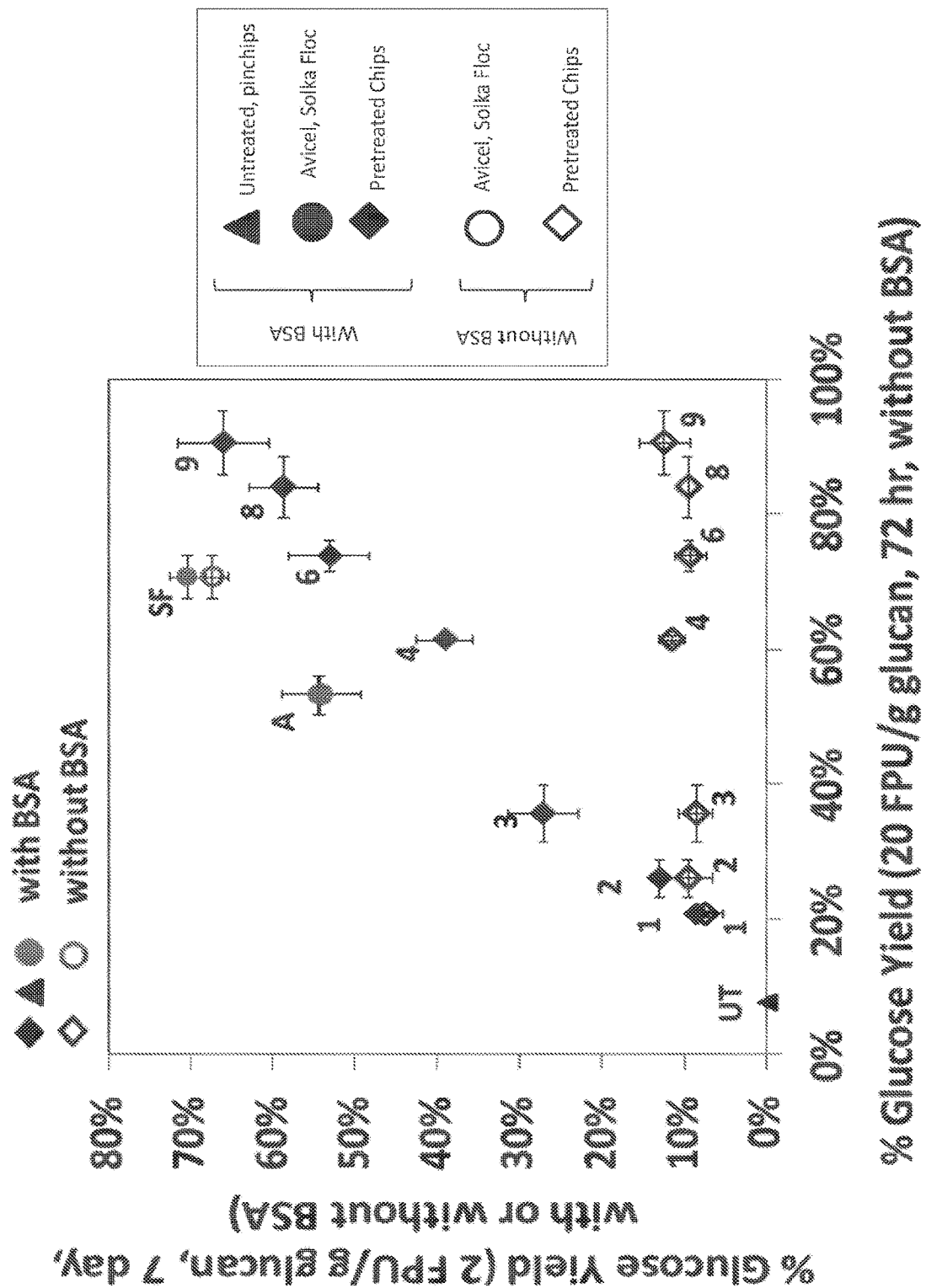
FIG. 7A shows the effect of BSA treatment on low-dose cellulase (2 FPU=3 mg protein/g glucan) hydrolysis of mixed hardwood pretreated at various conditions (see Table 1 for pretreatment conditions corresponding to each number). Low-dose cellulase hydrolysis yields (with or without BSA) are plotted against high-dose cellulose hydrolysis yields without BSA for each corresponding pretreatment condition. Data are average of triplicate analysis. Error bars represent 95% CI.
Figure 7B:
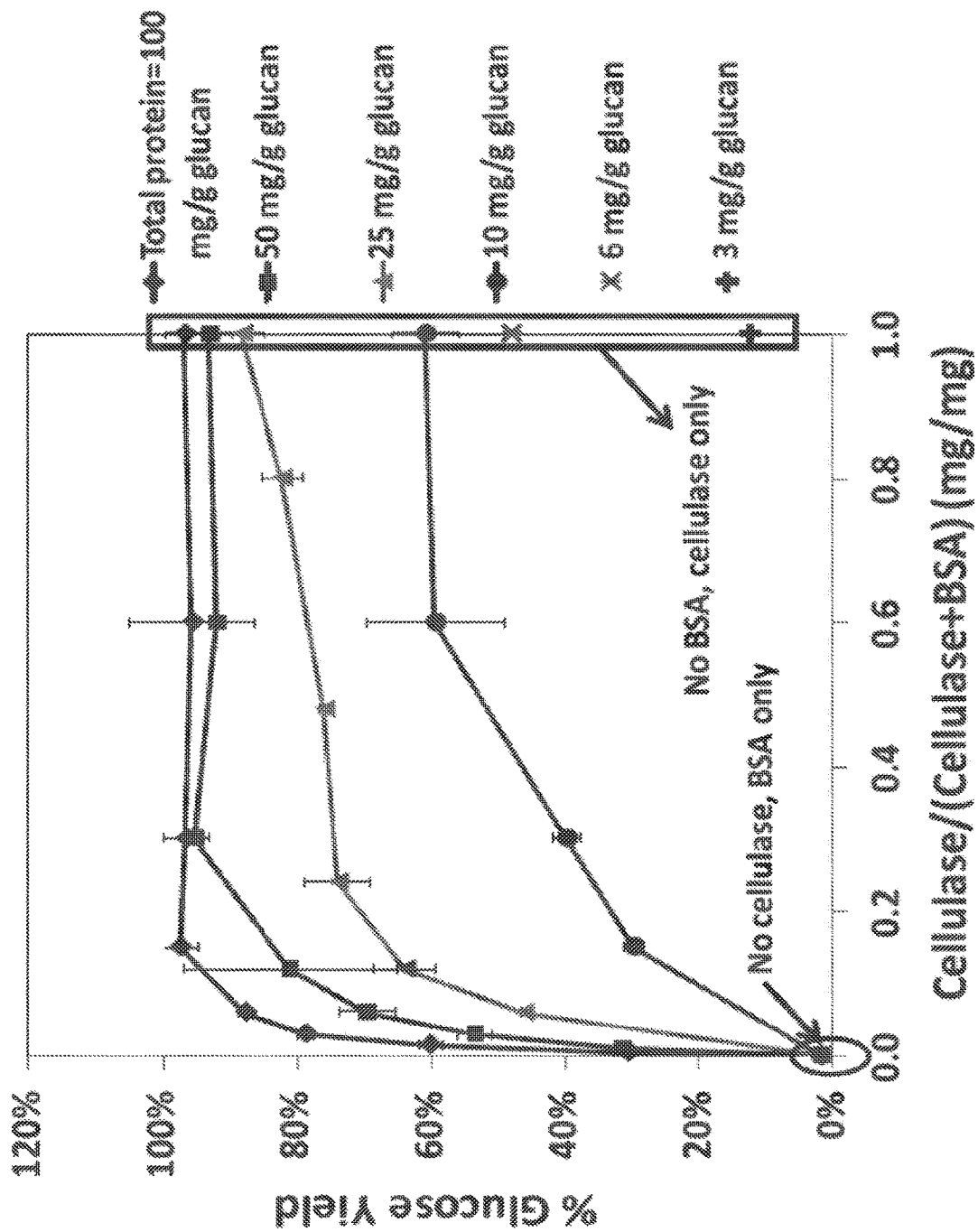
FIG. 7B shows the effect of varying ratio of cellulase to total proteins (BSA+cellulase) on hydrolysis of pretreated, hot-water washed mixed hardwood (sample 9 in Table 1). Data is average of triplicate analysis. Error bars represent 95% CI.

The severely pretreated sample 9 exhibited a high yield (approximately 70%) with low cellulose dose (2 FPU/g glucan) when lignin was blocked with BSA at 150 mg BSA per g glucan as shown in FIG. 7A. This indicated that the pretreated substrate exhibited favorable substrate characteristics for high enzyme accessibility to cellulose if non-specific lignin-cellulase binding was eliminated by BSA treatment as discussed in previous sections. The sample 9 was chosen to further determine the minimum requirement of necessary total protein loadings of BSA and cellulase for achieving high yields (>90N. It is critical to estimate the amount of total proteins and the ratio of cellulose to lignin-blocking non-cellulolytic proteins such as BSA as these ultimately determine the cost of proteins in lignocelluloses conversion process and economical feasibility of such process. The ratio of cellulase to total protein (BSA and cellulose combined) was varied at 4 different total protein levels (10-100 mg total protein/g glucan). At each total protein level, the amount of cellulase (Spezyme CP) was varied to give different ratios of cellulase to total protein (cellulase/cellulase+BSA). Hydrolysis yields were plotted against the ratios of cellulase to total protein as presented in FIG. 7B.

When there was only BSA, yield was only 2%. When only cellulase was added without BSA (at cellulase total protein ratio=1), yields varied between 13-97%, 3 mg protein/glucan giving the lowest yield (13%) and 100 mg protein/g glucan resulting in near 100% glucose yield. When cellulase loading was greater than 25 mg protein/g glucan, the yield was close to 90% even without any BSA treatment (see ratio=1 in FIG. 7B), indicating that, at above 25 mg cellulase proteins/g glucan, the available cellulase proteins for efficient hydrolysis are enough to overcome the loss of cellulase proteins by non-specific binding between cellulase and lignin.

At 100 mg cellulase protein/g glucan, replacing 85 mg cellulose protein with the same amount of BSA (cellulose loading=15 mg/g glucan, equivalent to cellulose to total protein ratio=0.15) resulted in the same yield (97%) as the hydrolysis with 100 mg cellulose protein/g glucan. At 3 mg cellulose protein and 97 mg BSA (cellulose to total protein ratio=0.03), the yield was close to 80%. Similarly, at 50 mg total protein loading, 6 mg cellulose and 44 mg BSA per g glucan (cellulose to total protein ratio=0.12) resulted in 81% glucose yield. Considering that at least 25 mg cellulase protein/g glucan was necessary to give the similar extent of cellulose conversion when BSA was not added, theses indicates that the amount of cellulase loading can be greatly reduced (from 25 to 3 mg protein/g glucan) if lignin is efficiently blocked by BSA. The ratio of cellulase to total proteins that corresponded to 80% glucose yield was 0.03, 0.12 and 0.8 for 100, 50 and 25 mg total protein/g glucan loadings, respectively. The results indicated that at least greater than 50 mg BSA per g glucan was required to extensively block the lignin to ensure a high cellulose conversion (>80%) at a low cellulase loading (<6 mg cellulase/g glucan).

Those skilled in the art will recognize that numerous modifications can be made to the specific implementations described above. The implementations should not be limited to the particular limitations described. Other implementations may be possible. In addition, all references cited herein are indicative of the level of skill in the art and are hereby incorporated by reference in their entirety.

1. Kim Y, Hendrickson R, Mosier N S, Ladisch M R. 2009. Liquid hot water pretreatment of cellulosic biomass. In: Mielenz J R, editor. Methods in Molecular Biology: Biofuels. Totowa: The Humana Press. 581: p 93-102.
2. Weil J, Westgate P J, Kohlmann K L, Ladisch M R. 1994. Cellulose pretreatments of lignocellulosic substrates. Enz Microb Technol 16:1002-1004.
3. Ladisch M R, Kohlmann K, Westgate P, Weil J, Yang Y. 1998. Processes for treating cellulosic material. U.S. Pat. No. 5,846,787.
4. Söderström J, Galbe M, Zacchi G. 2004. Effect of washing on yield in one- and two-step steam pretreatment of softwood for production of ethanol. Biotechnol Prog 20:744-749.
5. Nguyen Q A, Tucker M P, Keller F A, Eddy F P. 2000. Two-stage dilute acid pretreatment of softwoods. Appl Biochem Biotechnol 84-86:561-576,
6. Kim Y, Kreke T, Ladisch M R. xx. A systematic approach to understand the yield-determining substrate characteristics of liquid hot water pretreated lignocellulose. Part I: Assessment of efficiencies of single and multi-stage pretreatments of mixed hardwood. Biotechnol Bioeng xx:xx-xx.
7. Chandra R P, Bura R, Mabee W E, Berlin A, Pan X, Saddler J N. 2007. Substrate pretreatment: The key to effective enzymatic hydrolysis of lignocellulosics? Adv Biochem Eng Biotechnol 108:67-93
8. Chang V S, Holtzapple M T. 2000. Fundamental factors affecting biomass enzymatic reactivity. Appl Biochem Biotechnol 84-86:5-37.
9. Zhang Y H P, Lynd L. 2004. Toward an aggregated understanding of enzymatic hydrolysis of cellulose: Non-complexed cellulase systems. Biotechnol Bioeng 88:797-824.
10. Zhu Z, Sathitsuksanoh N, Vinzant T, Schell D J, McMillan J D, Zhang Y H. 2009. Comparative study of corn stover pretreated by dilute acid and cellulose solvent-based lignocellulose fractionation: Enzymatic hydrolysis, supramolecular structure, and substrate accessibility. Biotechnol Bioeng 103:715-24,
11. Kumar R, Wyman C E. 2009. Access of cellulase to cellulose and lignin for poplar solids produced by leading pretreatment technologies. Biotechnol Prog 25:807-819.
12. Rollin J A, Zhu Z, Sathitsuksanoh N, Zhang Y H P. 2011. Increasing cellulose accessibility is more important than removing lignin: A comparison of cellulose solvent-based lignocellulose fractionation and soaking in aqueous ammonia. Biotechnol Bioeng 108:22-30.
13. Del Rio L F, Chandra R P, Saddler J N. 2011. The effects of increasing swelling and anionic charges on the enzymatic hydrolysis of organosolv-pretreated softwoods at low enzyme loadings. Biotechnol Bioeng 108:1549-1558.
14. Arantes V, Saddler J N. 2011. Cellulose accessibility limits the effectiveness of minimum cellulase loading on the efficient hydrolysis of pretreated lignocellulosic substrates. Biotechnol Biofuels 4:3.
15. Jeoh T, Ishizawa C, Davis M F, Himmel M E, Adney W, Johnson D K. 2007. Cellulase digestibility of pretreated biomass is limited by cellulose accessibility. Biotechnol Bioeng 98: 112-122.

16. Puri V P. 1984. Effect of crystallinity and degree of polymerization of cellulose on enzymatic saccharification. Biotechnol Bioeng 26:1219-1222
17. Caulfield D F, Moor W E. 1974. Effect of varying crystallinity of cellulose on enzymic hydrolysis. Wood Sci 6:375-379.
18. Huang R, Su R, Qi W, He Z. 2010. Understanding the key factors for enzymatic conversion of pretreated lignocellulose by partial least square analysis. Biotechnol Prog 26:384-392.
19. Kumar R, Mago G, Balan V, Wyman C E. 2009. Physical and chemical characterizations of corn stover and polar solids resulting from leading pretreatment technologies. Bioresour Technol 100:3948-3962.
20. Hames B D. 1981. Gel electrophoresis of proteins: a practical approach. Hames B D, Rickwood D, editors. Washington D.C.: IRL Press. p 1-92.
21. Ehrman T. 1994. Standard method for the determination of extractives in biomass. Chemical analysis and testing task laboratory analytical procedures, NREL Ethanol Project.
22. Ehrman T. 1994. Standard method for ash in biomass, Chemical analysis and testing task laboratory analytical procedures. NREL Ethanol Project.
23. Sluiter A, Hames B, Ruiz R, Scarlata C, Sluiter J, Templeton D, Crocker D. 2006. Determination of structural carbohydrates and lignin in biomass. Biomass analysis technology team laboratory analytical procedures. NREL Biomass Program.
24. Sluiter A, Hames B, Ruiz R, Scarlata C, Sluiter J, Templeton D. 2005. Determination of sugars, byproducts, and degradation products in liquid fraction process samples. Biomass analysis technology team laboratory analytical procedures (LAP 014). NREL Biomass Program.
25. Chandra R, Ewanick S, Hsieh C, Saddler J N. 2008. The characterization of pretreated lignocellulosic substrates prior to enzymatic hydrolysis, part 1: A modified Simons' staining technique. Biotechnol Prog 24:1178-1185.
26. Hubbell C A, Ragauskas A J. 2010. Effect of acid-chlorite delignification on cellulose degree of polymerization. Bioresour Technol 101:7410-7415.
27. ASTM. 1986, Standard Test Methods for Intrinsic Viscosity of Cellulose (D 1795). American Society for Testing Materials 15.04. p 360-366.
28. Heiningen A V, Tunc M S, Gao Y, Perez D D S. 2004. Relationship between alkaline pulp yield and the mass fraction and degree of polymerization of cellulose in pulp. J Pulp Pap Sci 30:211-217
29. TAPPI. 1991. TAPPI useful method UM256. Water retention value (WRV), TAPPI Useful Methods, TAPPI Press. Atlanta, USA. www.Tappi.org
30. Wong K K Y, Deverell K F, Mackie K L, Clark T A, Donaldson L A. 1988. The relationship between fiber porosity and cellulose digestibility in steam exploded *Pinus radiata*. Biotechnol Bioeng 31:447-456.
31. Burns D S, Ooshima H, Converse A O. 1989. Surface area of pretreated lignocellulosics as a function of the extent of enzymatic hydrolysis. Appl Biochem Biotechnol 20-21:79-94.
32. Wang Q Q, Zhu Z H, Zhang Y H P, Ni Y, Luo X L, Zhu J Y. 2012. Evaluations of cellulose accessibilities of lignocelluloses by solute exclusion and protein adsorption techniques. Biotechnol Bioeng 109:381-389
33. Chandra R P, Esteghlalian A R, Saddler J N. 2008. Assessing substrate accessibility to enzymatic hydrolysis by cellulases. In: Hu T Q, editor. Characterization of lignocellulosic materials. Oxford: Blackwell. p 60-80.
34. Ogiwara Y, Arai K. 1969. Change in degree of polymerization of wood pulp with cellulase hydrolysis. Text Res J 39:422-427.
35. Luo X, Zhu J Y. 2011. Effects of drying-induced fiber hornification on enzymatic saccharification of lignocelluloses. Enzyme Microb Tech 48:92-99.
36. Yu X. Atalla R H. 1998. A staining technique for evaluating the pore structure variations of microcrystalline cellulose powders. Power Technol 98:135-138.
37. Cowling E B, Kirk T K. 1976. Properties of cellulose and lignocellulosic materials as substrates for enzymatic conversion processes. Biotech Bioeng Symp 6:95-123.
38. Welmer P J, Weston W M. 1985. Relationship between the fine structure of native cellulose and cellulose degradability by the cellulase complexes of *Trichoderma reesei* and *Clostridium thermocellum*. Biotechnol Bioeng 27:1540-1547.
39. Grethlein H E. 1985. The effect of pore size distribution on the rate of enzymatic hydrolysis of cellulosic substrates. Biotechnol 2:155-160.
40. Chandra R P, Ewanick S M, Chung P A, Au-Yeung K, Del Rio L, Mabee W, Saddler J N. 2009. Comparison of methods to assess the enzyme accessibility and hydrolysis of pretreated lignocellulosic substrates, Biotechnol Lett 31:1217-1222.
41. Teghammar A, Chandra R, Saddler J N, Taherzadeh M J, Horváth IS. 2012. Substrate characteristic analysis for anaerobic digestion: a study on rice and triticale straw. BioResources.com 7:3921-3934.
42. Yang B, Wyman C E. 2006. BSA treatment to enhance enzymatic hydrolysis of cellulose in lignin containing substrates. Biotechnol Bioeng 5:611-617.
43. Ishizawa C, Davis M F, Schell D F, Johnson D K. 2007. Porosity and its effect on the digestibility of dilute sulfuric acid pretreated corn stover. J Agric Food Chem 55:2575-2581.
44. Mansfield S D, Mooney C, Saddler J N. 1999. Substrate and enzyme characteristics that limit cellulose hydrolysis. Biotechnol Prog 15:804-816.
45. Vidal Jr B C, Dien B S, Ting K C, Singh V. 2011. Influence of feedstock particle size on lignocellulose conversion. Appl Biochem Biotechnol 164:1405-1421.
46. Laivins G V, Scallan A M. 1996. The influence of drying and beating on the swelling of fines. J Pulp Paper Sci 5:J178-J184.
47. Walseth C S. 1952. The influence of the fine structure of cellulose on the action of cellulases. Tappi J 35:233-236.
48. Lee Y H. 1981. Kinetic studies of enzymatic hydrolysis of insoluble cellulose: (II). Analysis of extended hydrolysis times. Biotechnol Bioeng 25:9:39-966.
49. Mooney C A, Mansfield S D, Touhy M G, Saddler J N. 1998. The effect of initial pore volume and lignin content on the enzymatic hydrolysis of softwoods. Bioresour Technol 64:113-119,
50. Pan X, Xie D, Yu R W, Lam D, Saddler J N, 2007. Pretreatment of lodgepole pine killed by mountain pine beetle using the ethanol organosolv process: Fractionation and process optimization. Ind Eng Chem Res 46:2609-2617.
51. Sinitsyn A P, Gusakov A V, Vlasenko E Y. 1991. Effect of structural and physicochemical features of cellulosic substrates on the efficiency of enzymatic hydrolysis. Appl Biochem Biotechnol 30:43-59
52. Del Rio L F, Chandra R P, Saddler J N. 2010, The effect of varying organosolv pretreatment chemicals on the physicochemical properties and cellulolytic hydrolysis of mountain pine beetle-killed lodge pole pine. Appl Biochem Biotechnol 161:1-21.
53. Ucar G, Fengel D. 1988. Characterization of the acid pretreatment for the enzymatic-hydrolysis of wood. Holz-forschung 42:141-148.
54. Hallac B B, Ragauskas J. 2011. Analyzing cellulose degree of polymerization and its relevancy to cellulosic ethanol. Biofuels Bioprod Bioref 5:215-225.
55. Pan A, Xie D, Kang K Y, Yoon S L, Saddler J N. 2007. Effect of organosolv ethanol pretreatment variables on physical characteristics of hybrid poplar substrates. Appl Biochem Biotechnol 136-140:367-377.
56. Battista A, Coppicio S, Howsmon J A, Morehead F F, Sisson W A. 1956. Level-off degree of polymerization relation to polyphase structure of cellulose fibers. Ind Eng Chem 48:333-335.
57. Kwiatkowski J R, McAloon A J, Taylor F, Johnston D B. 2006. Modeling of the process and costs of fuel ethanol production by corn dry grind process. Ind Crop Prod 23:288-296.
58. Kim Y, Ximenes E, Mosier N S, Ladisch M R. 2011. Soluble inhibitors/deactivators of cellulase enzymes from lignocellulosic biomass. Enzyme Microb Tech 48:408-415.
59. Ximenes E, Kim Y, Mosier N S, Dien B, Ladisch M R. 2011. Deactivation of cellulases by phenols. Enzyme Microb Tech 48:54-60.
60. Ximenes E, Kim Y, Mosier N S, Dien B, Ladisch M R. 2010. Inhibition of cellulase by phenols. Enzyme Microb Tech 46:170-176.
61. Kim Y, Kreke T, Hendrickson R, Parenti J, Ladisch M R. 2012, Fractionation of cellulose and fermentation inhibitors from steam pretreated mixed hardwood. Bioresour Technol In press.
62. Selig M J, Viamajala S, Decker S R, Tucker M P, Himmel M E, Vinzant T B. 2007. Deposition of lignin droplets produced during dilute acid pretreatment of maize stems retards enzymatic hydrolysis of cellulose. Biotechnol Prog 23:1333-1339,
63. Pan X, Xie D, Gilkes N, Gregg D J, Saddler J N. 2005. Strategies to enhance the enzymatic hydrolysis of pretreated softwood with high residual lignin content. Appl Biochem Biotechnol 124:1069-1079.
64. Ash M, Ash, I. 2007, Handbook of fillers, extenders, and diluents, $2^{nd}$ edition. Synapse information Resources, Inc. NY, USA. p 22, 173.
65. Fan, L T, Lee, Y H, H, D. 1980. Mechanism of the enzymatic hydrolysis of cellulose: effects of major structural features of cellulose on enzymatic hydrolysis. Biotechnol Bioeng 22:177-199.
66. Medve J, Lee D, Tjerneld F. 1998. Ion-exchange chromatographic purification and quantitative analysis of Trichoderma reesei cellulases cellobiohydrolase I, II and endoglucanase II by fast protein liquid chromatography. J Chromatogr A 808:153-165.
67, Ding S, Liu Y, Zeng Y, Himmel M E, Baker J O, Bayer E A. 2013. How does plant cell wall nanoscale architecture correlate with enzymatic digestibility? Science 338:1055:1060.
68. Kumar V, Kothari S H. 1999. Effect of compressional force on the crystallinity of directly compressible cellulose excipients. International Journal of Pharmaceutics 177:173-182.

The invention claimed is:
1. A method for improving enzymatic digestibility of lignocellulose, comprising:
pretreating a lignocellulose feedstock comprising cellulose, hemicellulose, and lignin with at least a two-step hydrothermal pretreatment to produce a pretreated lignocellulose feedstock, wherein the first hydrothermal pretreatment is conducted at a temperature above 140° C., and the second hydrothermal pretreatment is conducted at a temperature above 180° C., wherein the first and second hydrothermal pretreatments are each chosen from a liquid hot water treatment, a steam explosion treatment, and a dilute-acid treatment, and combinations thereof;
solubilizing at least 50% of the hemicellulose in the pretreated lignocellulose feedstock as xylo-oligosaccharides;
separating and washing the solids of the pretreated lignocellulose feedstock to thereby eliminate inhibition by soluble xylo-oligosaccharides and phenolic compounds released during pretreating;
forming a slurry of washed pretreated lignocellulose feedstock;
adding a lignin-blocking non-cellulolytic protein to the washed pretreated lignocellulose feedstock slurry to block the lignin retained in the washed pretreated lignocellulose feedstock from binding with a cellulase enzyme in an amount of at least 44 mg lignin-blocking non-cellulolytic protein/g glucan; and
adding a cellulase enzyme to the washed pretreated lignocellulose feedstock slurry in an amount of up to 6 mg cellulase/g glucan.
2. The method of claim 1, wherein the lignocellulose feedstock comprises a component of corn.
3. The method of claim 1, wherein the washing step further comprises using water of between about 0.5 to about 15 times the weight of the solids of the pretreated lignocellulose feedstock.
4. The method of claim 3, wherein the water is recycled water.
5. The method of claim 4, wherein the washing step further comprises using distillation column bottoms.
6. The method of claim 1, wherein the washing step is conducted at room temperature.
7. The method of claim 1, wherein the washing step is conducted at temperatures up to 140° C., wherein the washing step comprises pressure washing.
8. The method of claim 1, wherein the washing step is conducted at temperatures up to 100° C.
9. The method of claim 1, wherein the washing step is carried out in a plurality of stages, wherein the washed pretreated lignocellulose feedstock from the second washing stage is contacted counter-currently with wash water from the first washing stage.
10. The method of claim 1, wherein the pretreating step comprises at least a three-step hydrothermal pretreatment, wherein the first hydrothermal pretreatment is conducted at a temperature above 140° C., and the second hydrothermal pretreatment and third hydrothermal pretreatment are conducted at temperatures above 180° C.
11. The method of claim 1, wherein the lignin-blocking non-cellulolytic protein comprises bovine serum albumin (BSA).
12. The method of claim 1, wherein the lignocellulose feedstock is selected from the group consisting of hardwood, corn stover, wheat straw, switchgrass, sugarcane bagasse, sorghum residues, corn pericarp, soybean residue, hay, and softwoods, and combinations thereof.

13. The method of claim 1, wherein the lignocellulose feedstock comprises at least one of corn stover and corn pericarp.

14. The method of claim 1, wherein the cellulase enzyme loading is in the range of 3-6 mg cellulase/g glucan and the lignin-blocking non-cellulolytic protein loading is in the range of 44-97 mg lignin-blocking non-cellulolytic protein/g glucan.

15. The method of claim 1, wherein adding the lignin-blocking non-cellulolytic binding protein to the washed pretreated lignocellulose feedstock is in an amount of at least 50 mg lignin-blocking non-cellulolytic protein/g glucan.

16. The method of claim 1, wherein during the adding steps the pH of the slurry is maintained in the range of 4.8 to 5.0.

17. The method of claim 1, wherein said solubilizing is accomplished by pretreatment with liquid hot water under pressure to maintain the hot water in a liquid state.

18. The method of claim 17, wherein said lignocellulose feedstock has a composition of 30-60% cellulose, 20 to 40% hemicellulose, and 15 to 30% lignin, with the balance extractives and ash to give a total of 100%.

19. The method of claim 18, wherein said separating and washing the solids of the pretreated lignocellulose feedstock comprises separating and washing with 1 to 20 volumes of water per volume lignocellulose.

20. The method of claim 1, wherein the first and second hydrothermal pretreatments are liquid hot water treatment.

\* \* \* \* \*